(12) United States Patent
Cheng et al.

(10) Patent No.: US 11,813,109 B2
(45) Date of Patent: Nov. 14, 2023

(54) DERIVING INSIGHTS INTO HEALTH THROUGH ANALYSIS OF AUDIO DATA GENERATED BY DIGITAL STETHOSCOPES

(71) Applicant: Heroic Faith Medical Science Co., Ltd., New Taipei (TW)

(72) Inventors: Yuan Ren Cheng, New Taipei (TW); Fushun Hsu, New Taipei (TW); Ji-De Huang, New Taipei (TW); Shang-Ran Huang, New Taipei (TW)

(73) Assignee: Heroic Faith Medical Science Co., Ltd., New Taipei (TW)

( * ) Notice: Subject to any disclaimer, the term of this patent is extended or adjusted under 35 U.S.C. 154(b) by 0 days.

(21) Appl. No.: 18/055,278

(22) Filed: Nov. 14, 2022

(65) Prior Publication Data

US 2023/0076296 A1    Mar. 9, 2023

Related U.S. Application Data

(63) Continuation of application No. PCT/US2021/032595, filed on May 14, 2021.

(60) Provisional application No. 63/025,395, filed on May 15, 2020.

(51) Int. Cl.
*A61B 5/08* (2006.01)
*A61B 7/00* (2006.01)
*A61B 5/00* (2006.01)

(52) U.S. Cl.
CPC ............ *A61B 7/003* (2013.01); *A61B 5/0816* (2013.01); *A61B 5/7246* (2013.01); *A61B 5/7264* (2013.01); *A61B 5/7282* (2013.01)

(58) Field of Classification Search
CPC ..... A61B 7/003; A61B 5/0816; A61B 5/7246; A61B 5/7264; A61B 5/7282
See application file for complete search history.

(56) References Cited

U.S. PATENT DOCUMENTS

| | | | |
|---|---|---|---|
| 10,555,717 B2 | 2/2020 | Hsu et al. | |
| 2011/0075851 A1* | 3/2011 | LeBoeuf | G10L 25/51 |
| | | | 381/56 |
| 2017/0296094 A1 | 10/2017 | Fonzi et al. | |
| 2018/0085068 A1* | 3/2018 | Telfort | A61B 5/318 |
| 2019/0088367 A1* | 3/2019 | Stamatopoulos | G16H 50/20 |
| 2019/0159960 A1 | 5/2019 | Nakata et al. | |
| 2019/0272845 A1* | 9/2019 | Hasan | G16H 40/63 |

OTHER PUBLICATIONS

International Search Report and Written Opinion dated Aug. 30, 2021 for International Patent Application No. PCT/US21/32595 (15 pages).

* cited by examiner

*Primary Examiner* — Andrey Shostak
(74) *Attorney, Agent, or Firm* — Perkins Coie LLP

(57) ABSTRACT

Introduced here are computer programs and associated computer-implemented techniques for deriving insights into the health of patients through analysis of audio data generated by electronic stethoscope systems. A diagnostic platform may be responsible for examining the audio data generated by an electronic stethoscope system so as to gain insights into the health of a patient. The diagnostic platform may employ heuristics, algorithms, or models that rely on machine learning or artificial intelligence to perform auscultation in a manner that significantly outperforms traditional approaches that rely on visual analysis by a healthcare professional.

9 Claims, 18 Drawing Sheets

100

100

100

1500

1501
Obtain a vector that includes entries arranged in a temporal order

1502
Identify (i) a first breathing event, (ii) a second breathing event, and (iii) a third breathing event by examining the entries of the vector

1503
Determine (i) a first period between the first and second breathing events and (ii) a second period between the second and third breathing events

1504
Compute a respiratory rate based on the first and second periods

1505
Cause display of an interface that includes a spectrogram corresponding to the audio data

1506
Post the respiratory rate to the interface to facilitate diagnostic determination by a healthcare professional

1507
Compare the respiratory rate to a threshold

1508
Take appropriate action based on an outcome of the comparison

FIGURE 15

DERIVING INSIGHTS INTO HEALTH THROUGH ANALYSIS OF AUDIO DATA GENERATED BY DIGITAL STETHOSCOPES

CROSS-REFERENCE TO RELATED APPLICATIONS

This application is a continuation of International Application No. PCT/US2021/032595, filed on May 14, 2021, which claims priority to U.S. Provisional Application No. 63/025,395, filed on May 15, 2020, each of which is incorporated by reference herein in its entirety.

TECHNICAL FIELD

Various embodiments pertain to computer programs and associated computer-implemented techniques for deriving insights into the health of patients through analysis of audio data generated by electronic stethoscope systems.

BACKGROUND

Historically, acoustic stethoscopes have been used to listen to the internal sounds originating from within a living body. This process—referred to as "auscultation"—is normally performed for the purpose of examining biological systems whose performance can be inferred from these internal sounds. Normally, acoustic stethoscopes include a single chestpiece that has a resonator designed to be placed against the body and a pair of hollow tubes that are connected to earpieces. As sound waves are captured by the resonator, they are directed to the earpieces via the pair of hollow tubes.

But acoustic stethoscopes suffer from several drawbacks. For example, an acoustic stethoscope will attenuate the sound proportional to the frequency of the source. Thus, the sound conveyed to the earpieces tends to be very faint, which can make it difficult to accurately diagnose conditions. In fact, due to variation in sensitivity of the ear, some sounds (e.g., those below 50 hertz) may not be heard at all.

Some enterprises have begun developing electronic stethoscopes (also referred to as "stethophones") to address the drawbacks of acoustic stethoscopes. Electronic stethoscopes improve upon acoustic stethoscopes by electronically amplifying sounds. For instance, an electronic stethoscope may address the faint sounds originating inside a living body by amplifying these sounds. To accomplish this, the electronic stethoscope converts sound waves detected by a microphone located in the chestpiece into an electrical signal and then amplifies the electrical signal for optimal listening.

BRIEF DESCRIPTION OF THE DRAWINGS

FIG. 15 depicts a flow diagram of a process for computing the respiratory rate based on analysis of audio data containing sounds made by the lungs of a patient.

Figure 1A:
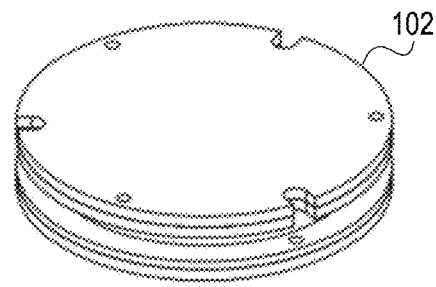
FIG. 1A includes a top perspective view of an input unit for an electronic stethoscope system.

Embodiments are illustrated by way of example and not limitation in the drawings. While the drawings depict various embodiments for the purpose of illustration, those skilled in the art will recognize that alternative embodiments may be employed without departing from the principles of the technology. Accordingly, while specific embodiments are shown in the drawings, the technology is amenable to various modifications.

DETAILED DESCRIPTION

Electronic stethoscope systems can be designed to simultaneously monitor sounds originating from inside and outside a living body under examination as further discussed below. As further discussed below, an electronic stethoscope system may include one or more input units that are connected to a hub unit. Each input unit may have a conical resonator that is designed to direct sound waves toward at least one microphone that is configured to produce audio data indicative of internal sounds originating inside the living body. These microphones may be referred to as "auscultation microphones." Moreover, each input unit may include at least one microphone that is configured to produce audio data indicative of external sounds originating outside the living body. These microphones may be referred to as "ambient microphones" or "environmental microphones."

For the purpose of illustration, an "ambient microphone" may be described as being capable of producing audio data indicative of "ambient sounds." However, these "ambient sounds" generally include a combination of external sounds produced by three different sources: (1) sounds originating from the ambient environment; (2) sounds that leak through the input unit; and (3) sounds that penetrate the living body under examination. Examples of external sounds include sounds that originate directly from the input unit (e.g., scratching by the finger or chest) and low-frequency environmental noises that penetrate the input unit.

There are several advantages to separately recording internal and external sounds. Notably, the internal sounds can be electronically amplified while the external sounds can be electronically dampened, attenuated, or filtered. Thus, the electronic stethoscope system may address the faint sounds originating from within the living body under examination by manipulating the audio data indicative of the internal and external sounds. Manipulation may result in undesirable digital artifacts that make it more difficult to interpret the internal sounds, however. For example, these digital artifacts may make it more difficult to identify patterns of values in the audio data generated by auscultation microphones that are indicative of inhalations or exhalations.

Introduced here are computer programs and associated computer-implemented techniques for deriving insights into the health of patients through analysis of audio data generated by electronic stethoscope systems. A diagnostic platform (also referred to as a "diagnostic program" or "diagnostic application") may be responsible for examining the audio data generated by an electronic stethoscope system so as to gain insights into the health of a patient. As further discussed below, the diagnostic platform may employ heuristics, algorithms, or models that rely on machine learning (ML) or artificial intelligence (AI) to perform auscultation in a manner that significantly outperforms traditional approaches that rely on visual analysis by a healthcare professional.

Assume, for example, that the diagnostic platform is tasked with inferring the respiratory rate of a patient based on audio data generated by an electronic stethoscope system that is connected to the patient. The term "respiratory rate" refers to the number of breaths taken per minute. For an adult at rest, a respiratory rate between 12 and 25 breaths per minute is considered normal. A respiratory rate that is less than 12 breaths per minute or greater than 25 breaths per minute while resting is considered abnormal. Because the respiratory rate is a key indicator of health, it is sometimes referred to as a "vital sign." As such, knowledge of the respiratory rate may be critical to providing appropriate care to the patient.

As mentioned above, the electronic stethoscope system may generate audio data that is indicative of internal sounds and audio data that is indicative of external sounds. The former may be referred to as "first audio data" or "internal audio data," and the latter may be referred to as "second audio data" or "external audio data." In some embodiments, the diagnostic platform utilizes the second audio data to improve the first audio data. Thus, the diagnostic platform may examine the second audio data to determine how, if at all, the first audio data should be manipulated to lessen the influence of external sounds. If, for example, the diagnostic platform discovers an external sound through analysis of the second audio data, the diagnostic platform may obtain and then apply a filter to the first audio data in an effort to remove the external sound without distorting internal sounds of interest (e.g., those corresponding to inhalations, exhalations, etc.). The filter may be generated by the diagnostic platform based on its analysis of the second audio data, or the filter may be identified (e.g., from amongst multiple filters) by the diagnostic platform based on its analysis of the second audio data.

Then, the diagnostic platform can apply a computer-implemented model (or simply "model") to the first audio data. The model may be designed and trained to identify the distinct phases of breathing, namely, inhalation and exhalation. The model may be a deep learning model that is based on one or more artificial neural networks (or simply "neural networks"). A neural network is a framework of ML algorithms that work together to process complex inputs. Inspired by the biological neural networks that constitute human and animal brains, neural networks can "learn" to perform tasks by considering examples without being programmed with task-specific rules. For example, a neural network may learn to identify inhalations and exhalations by examining series of audio data that have been labeled as "inhalation," "exhalation," or "no inhalation or exhalation." These series of audio data may be referred to as "training data." This approach to training allows the neural network to automatically learn features whose presence is indicative of inhalation and exhalation from the series of audio data. For example, the neural network may come to understand the patterns of values in audio data that are indicative of an inhalation, as well as the patterns of values in audio data that are indicative of an exhalation.

While outputs produced by the model may be helpful, those outputs can be difficult to interpret. For example, the diagnostic platform may generate a visual representation (also referred to as a "visualization") of the first audio data for review by a healthcare professional who is responsible for monitoring, examining, or diagnosing the patient. The diagnostic platform may visually highlight inhalations or exhalations in an effort to improve comprehensibility of the visualization. For example, the diagnostic platform may overlay a digital element (also referred to as a "graphical element") on the visualization to indicate that the patient took a breath. As further discussed below, the digital element may extend from the beginning of the inhalation as determined by the model to the end of the exhalation as determined by the model. By explaining the outputs produced by the model in a more comprehensible manner, the diagnostic platform can build trust with the healthcare professionals who rely on those outputs.

Moreover, the diagnostic platform may utilize outputs produced by the model to gain insights into the health of the patient. Assume, for example, that a model is applied to audio data associated with a patient in order to identify inhalations and exhalations as discussed above. In such a scenario, the diagnostic platform may utilize those outputs to produce metrics. One example of such a metric is respiratory rate. As mentioned above, the term "respiratory rate" refers to the number of breaths taken per minute. However, counting the actual number of breaths taken over the last minute is simply not practical. Significant irreversible damage may occur if the patient suffers anoxia for even limited amounts of time. Therefore, it is important that healthcare professionals have consistent insight into the respiratory rate that is updated in near real time. To accomplish this, the diagnostic platform may calculate the respiratory rate on an ongoing basis using a sliding window algorithm. At a high level, the algorithm defines a window that contains a portion of audio data and then continually slides the window to cover different portions of audio data. As further discussed below, the algorithm may adjust the window so that a predetermined number of inhalations or exhalations are always contained within its bounds. For example, the algorithm may be programmed such that three inhalations must be included within the bounds of the window, where the first inhalation represents the "beginning" of the window and the third inhalation represents the "ending" of the window. The diagnostic platform can then compute the respiratory rate based on the spacing between the inhalations included in the window.

For the purpose of illustration, embodiments may be described in the context of instructions that are executable by a computing device. However, aspects of the technology can be implemented via hardware, firmware, software, or any combination thereof. As an example, a model may be applied to audio data generated by an electronic stethoscope system in order to identify outputs that are representative of inhalations and exhalations of a patient. Then, an algorithm may be applied to the outputs produced by the model in order to produce a metric that indicates the respiratory rate of the patient.

Embodiments may be described with reference to particular computing devices, networks, and healthcare professionals and facilities. However, those skilled in the art will recognize that the features of those embodiments are similarly applicable to other computing devices, networks, and healthcare professionals and facilities. For example, while embodiments may be described in the context of a deep neural network, the model employed by the diagnostic platform may be based on another deep learning architecture, such as deep belief networks, recurrent neural networks, and convolutional neural networks.

Terminology

Brief definitions of terms, abbreviations, and phrases used throughout the application are given below.

The terms "connected," "coupled," and any variants thereof are intended to include any connection or coupling between two or more elements, either direct or indirect. The connection or coupling can be physical, logical, or a combination thereof. For example, objects may be electrically or communicatively connected to one another despite not sharing a physical connection.

The term "module" may be used to refer broadly to components implemented via software, firmware, hardware, or any combination thereof. Generally, modules are functional components that generate one or more outputs based on one or more inputs. A computer program may include one or more modules. Thus, a computer program may include multiple modules responsible for completing different tasks or a single module responsible for completing all tasks.

Overview of Electronic Stethoscope System

FIG. 1A includes a top perspective view of an input unit 100 for an electronic stethoscope system. For convenience, the input unit 100 may be referred to as a "stethoscope patch," even though the input unit may only include a subset of the components necessary for auscultation. The input unit 100 may also be referred to as a "chestpiece" since it will often be affixed to the chest of a body. However, those skilled in the art will recognize that the input unit 100 may be affixed to other parts of the body as well (e.g., the neck, abdomen, or back).

As further described below, the input unit 100 can collect sound waves that are representative of biological activities within a body under examination, convert the sound waves into an electrical signal, and then digitize the electrical signal (e.g., for easier transmission, to ensure higher fidelity, etc.). The input unit 100 can include a structural body 102 that is comprised of a rigid material. Normally, the structural body 102 is comprised of metal, such as stainless steel, aluminum, titanium, or a suitable metal alloy. To make the structural body 102, molten metal will typically be die-cast and then either machined or extruded into the appropriate form.

In some embodiments, the input unit 100 includes a casing that inhibits exposure of the structural body 102 to the ambient environment. For example, the casing may prevent contamination, improve cleanability, etc. Generally, the casing encapsulates substantially all of the structural body 102 except for the conical resonator disposed along its bottom side. The conical resonator is described in greater depth below with respect to FIGS. 1B-C. The casing may be comprised of silicon rubber, polypropylene, polyethylene, or any other suitable material. Moreover, in some embodiments, the casing includes an additive whose presence limits microbial growth, ultraviolet (UV) degradation, etc.

Figure 1B:
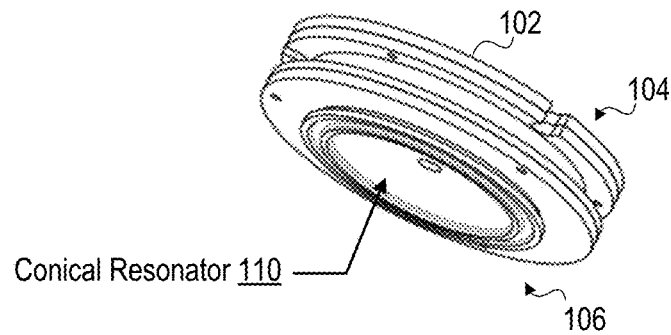
FIGS. 1B-C include bottom perspective views of the input unit shown in FIG. 1A.
Figure 1C:
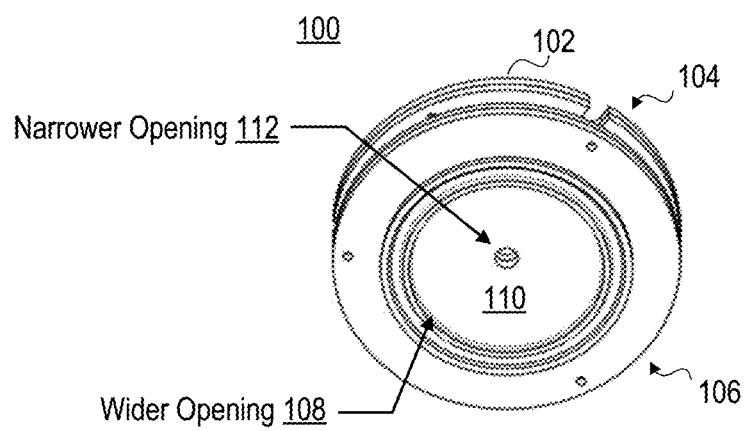

FIGS. 1B-C include bottom perspective views of the input unit 100, which includes a structural body 102 having a distal portion 104 and a proximal portion 106. To initiate an auscultation procedure, an individual (e.g., a healthcare professional, such as a physician or nurse) can secure the proximal portion 106 of the input unit 100 against the surface of a body under examination. The proximal portion 106 of the input unit 100 can include the wider opening 108 of a conical resonator 110. The conical resonator 110 may be designed to direct sound waves collected through the wider opening 108 toward a narrower opening 112, which may lead to an auscultation microphone. Conventionally, the wider opening 108 is approximately 30-50 millimeters (mm), 35-45 mm, or 38-40 mm. However, because the input unit 100 described here may have automatic gain control functionality, smaller conical resonators may be used. For example, in some embodiments, the wider opening 108 is less than 30 mm, 20 mm, or 10 mm. Thus, the input units described herein may be able to support a wide variety of conical resonators having different sizes, designed for different applications, etc.

With regard to the terms "distal" and "proximal," unless otherwise specified, the terms refer to the relative positions of the input unit 100 with reference to the body. For example, in referring to an input unit 100 suitable for fixation to the body, "distal" can refer to a first position close to where a cable suitable for conveying digital signals may be connected to the input unit 100 and "proximal" can refer to a second position close to where the input unit 100 contacts the body.

Figure 2:
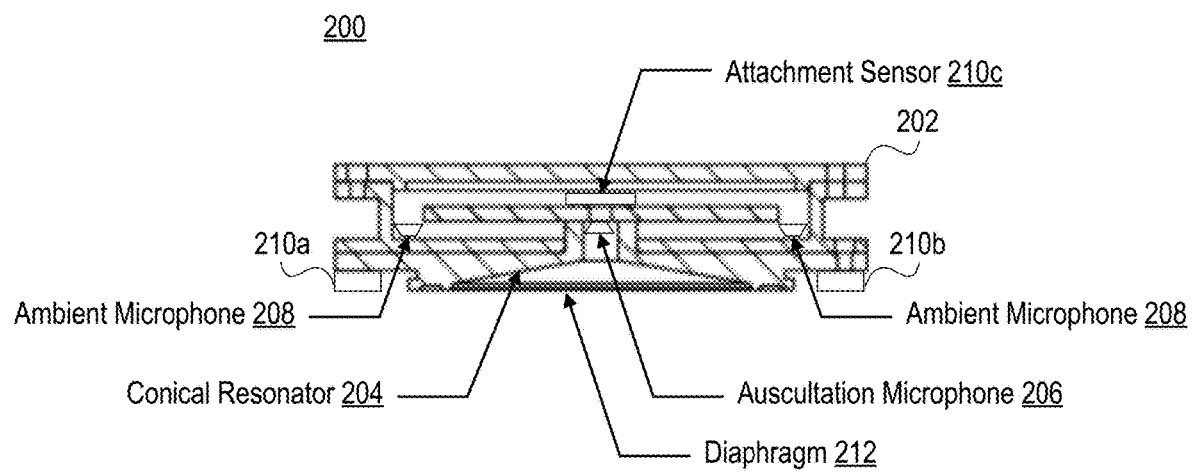
FIG. 2 includes a cross-sectional side view of an input unit for an electronic stethoscope system.

FIG. 2 includes a cross-sectional side view of an input unit 200 for an electronic stethoscope system. Often, the input unit 200 includes a structural body 202 having an interior cavity defined therein. The structural body 202 of the input unit 200 may have a conical resonator 204 designed to direct sound waves toward a microphone residing within the interior cavity. In some embodiments, a diaphragm 212 (also referred to as a "vibration film") extends across the wider opening (also referred to as the "outer opening") of the conical resonator 204. The diaphragm 212 can be used to listen to high-pitched sounds, such as those often produced by the lungs. The diaphragm 212 can be formed from a thin plastic disk comprised of an epoxy-fiberglass compound or glass fibers.

To improve the clarity of sound waves collected by the conical resonator 204, the input unit 200 may be designed to simultaneously monitor sounds originating from different locations. For example, the input unit 200 may be designed to simultaneously monitor sounds originating from within a body under examination and sounds originating from the ambient environment. Thus, the input unit 200 may include at least one microphone 206 (referred to as an "auscultation microphone") configured to produce audio data indicative of internal sounds and at least one microphone 208 (referred to as an "ambient microphone") configured to produce audio data indicative of ambient sounds. Each auscultation and ambient microphone may include a transducer able to convert sound waves into an electrical signal. Thereafter, the electrical signals produced by the auscultation and ambient microphones 206, 208 may be digitized prior to transmission to a hub unit. Digitization enables the hub unit to readily clock or synchronize the signals received from multiple input units. Digitization may also ensure that the signals received by the hub unit from an input unit have a higher fidelity than would otherwise be possible.

These microphones may be omnidirectional microphones designed to pick up sound from all directions or directional microphones designed to pick up sounds coming from a specific direction. For example, the input unit 200 may include auscultation microphone(s) 206 oriented to pick up sounds originating from a space adjacent to the outer opening of the conical resonator 204. In such embodiments, the ambient microphone(s) 208 may be omnidirectional or directional microphones. As another example, a set of ambient microphones 208 could be equally spaced within the structural body 202 of the input unit 200 to form a phased array able to capture highly directional ambient sounds to reduce noise and interference. Accordingly, the auscultation microphone(s) 206 may be arranged to focus on the path of incoming internal sounds (also referred to as the "auscultation path"), while the ambient microphone(s) 208 may be arranged to focus on the paths of incoming ambient sounds (also referred to as the "ambient paths").

Conventionally, electronic stethoscopes subjected electrical signals indicative of sound waves to digital signal processing (DSP) algorithms that were responsible for filtering undesirable artifacts. However, such action could suppress nearly all of the sound within certain frequency ranges (e.g., 100-800 Hz), thereby greatly distorting internal sounds of interest (e.g., those corresponding to inhalations, exhalations, or heartbeats). Here, however, a processor can employ an active noise cancellation algorithm that separately examines the audio data generated by the auscultation microphone(s) 206 and the audio data generated by the ambient microphone(s) 208. More specifically, the processor may parse the audio data generated by the ambient microphone(s) 208 to determine how, if at all, the audio data generated by the auscultation microphone(s) 206 should be modified. For example, the processor may discover that certain digital features should be amplified (e.g., because they correspond to internal sounds), diminished (e.g., because they correspond to ambient sounds), or removed entirely (e.g., because they represent noise). Such a technique can be used to improve the clarity, detail, and quality of sound recorded by the input unit 200. For example, application of the noise cancellation algorithm may be an integral part of the denoising process employed by an electronic stethoscope system that includes at least one input unit 200.

For privacy purposes, neither the auscultation microphone(s) 206 nor the ambient microphone(s) 208 may be permitted to record while the conical resonator 204 is directed away from the body. Thus, in some embodiments, the auscultation microphone(s) 206 and/or the ambient microphone(s) 208 do not begin recording until the input unit 200 is attached to the body. In such embodiments, the input unit 200 may include one or more attachment sensors 210a-c that are responsible for determining whether the structural body 202 has been properly secured to the surface of the body.

The input unit 200 could include any subset of the attachment sensors shown here. For example, in some embodiments, the input unit 200 includes only attachment sensors 210a-b, which are positioned near the wider opening of the conical resonator 204. As another example, in some embodiments, the input unit 200 includes only attachment sensor 210c, which is positioned near the narrower opening (also referred to as the "inner opening") of the conical resonator 204. Moreover, the input unit 200 may include different types of attachment sensors. For example, attachment sensor 210c may be an optical proximity sensor designed to emit light (e.g., infrared light) through the conical resonator 204 and then determine, based on the light reflected back into the conical resonator 204, the distance between the input unit 200 and the surface of the body. As another example, attachment sensors 210a-c may be audio sensors designed to determine, with the assistance of an algorithm programmed to determine the drop-off of a high-frequency signal, whether the structural body 202 is securely sealed against the surface of the body based on the presence of ambient noise (also referred to as "environmental noise"). As another example, attachment sensors 210a-b may be pressure sensors designed to determine whether the structural body 202 is securely sealed against the surface of the body based on the amount of applied pressure. Some embodiments of the input unit 200 include each of these different types of attachment sensors. By considering the output of these attachment sensor(s) 210a-c in combination with the aforementioned active noise cancellation algorithm, a processor may be able to dynamically determine the adhesion state. That is, the processor may be able to determine whether the input unit 200 has formed a seal against the body based on the output of these attachment sensors 210a-c.

Figure 3:
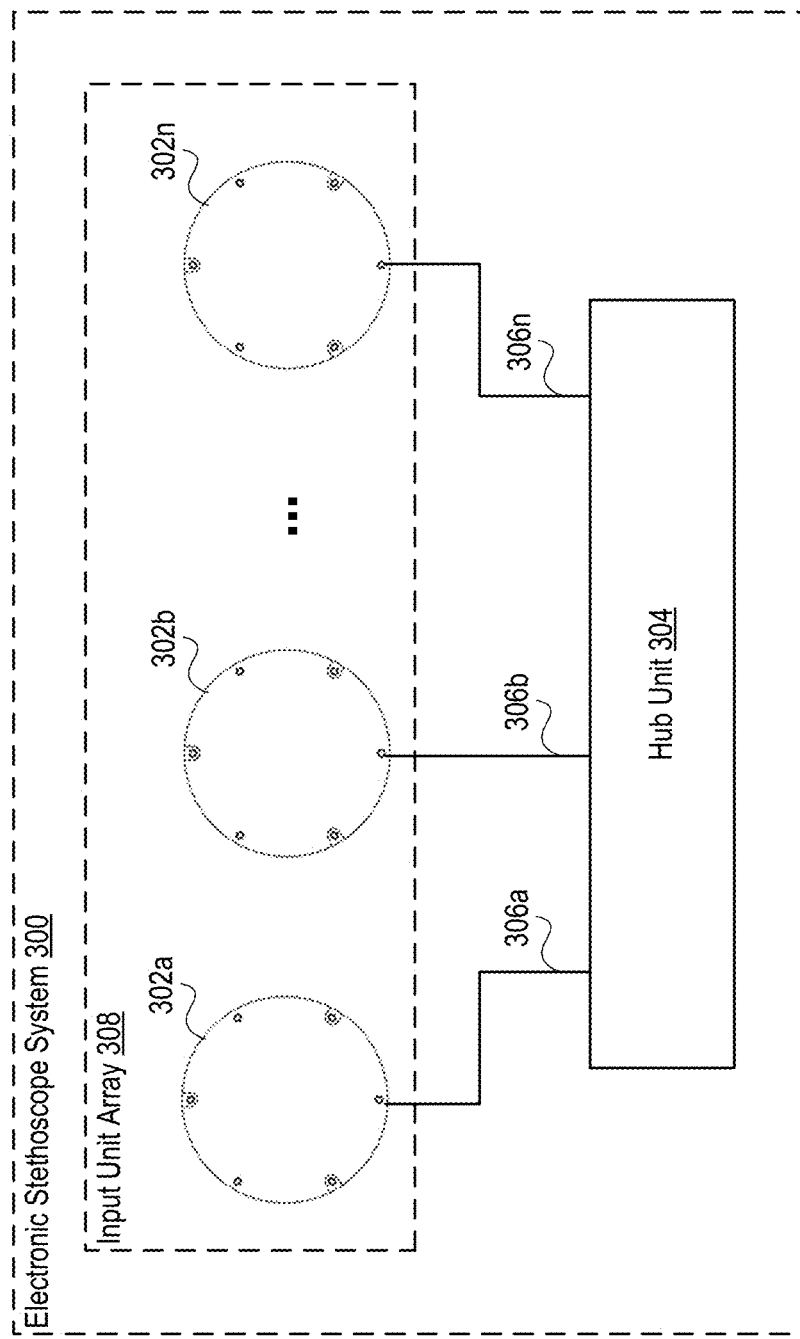
FIG. 3 illustrates how one or more input units can be connected to a hub unit to form an electronic stethoscope system.

FIG. 3 illustrates how one or more input units 302a-n can be connected to a hub unit 304 to form an electronic stethoscope system 300. In some embodiments, multiple input units are connected to the hub unit 304. For example, the electronic stethoscope system 300 may include four input units, six input units, or eight input units. Generally, the electronic stethoscope system 300 will include at least six input units. Electronic stethoscope systems that have multiple input units may be referred to as "multi-channel stethoscopes." In other embodiments, only one input unit is connected to the hub unit 304. For example, a single input unit may be moved across the body in such a manner as to simulate an array of multiple input units. Electronic stethoscope systems having one input unit may be referred to as "single-channel stethoscopes."

As shown in FIG. 3, each input unit 302a-n can be connected to the hub unit 304 via a corresponding cable 306a-n. Generally, the transmission path formed between each input unit 302a-n and the hub unit 304 via the corresponding cable 306a-n is designed to be substantially free of interference. For example, electronic signals may be digitized by the input units 302a-n prior to transmission to the hub unit 304, and signal fidelity may be ensured by prohibiting the generation/contamination of electromagnetic noise. Examples of cables include ribbon cables, coaxial cables, Universal Serial Bus (USB) cables, High-Definition Multimedia Interface (HDMI) cables, RJ45 ethernet cables, and any other cable suitable for conveying a digital signal. Each cable includes a first end connected to the hub unit 304 (e.g., via a physical port) and a second end connected to the corresponding input unit (e.g., via a physical port). Accordingly, each input unit 302a-n may include a single physical port, and the hub unit 304 may include multiple physical ports. Alternatively, a single cable may be used to connect all of the input units 302a-n to the hub unit 304. In such embodiments, the cable may include a first end capable of interfacing with the hub unit 304 and a series of second ends, each of which is capable of interfacing with a single input unit. Such a cable may be referred to, for example, as a "one-to-two cable," "one-to-four cable," or "one-to-six cable" based on the number of second ends.

When all of the input units 302a-n connected to the hub unit 304 are in an auscultation mode, the electronic stethoscope system 300 can employ an adaptive gain control algorithm programmed to compare internal sounds to ambient sounds. The adaptive gain control algorithm may analyze a target auscultation sound (e.g., normal breathing, wheezing, crackling, etc.) to judge whether an adequate sound level has been achieved. For example, the adaptive gain control algorithm may determine whether the sound level exceeds a predetermined threshold. The adaptive gain control algorithm may be designed to achieve gain control of up to 100 times (e.g., in two different stages). The gain level may be adaptively adjusted based on the number of input units in the input unit array 308, as well as the level of sound recorded by the auscultation microphone(s) in each input unit. In some embodiments, the adaptive gain control algorithm is programmed for deployment as part of a feedback loop. Thus, the adaptive gain control algorithm may apply gain to audio recorded by an input unit, determine whether the audio exceeds a preprogrammed intensity threshold, and dynamically determine whether additional gain is necessary based on the determination.

Because the electronic stethoscope system 300 can deploy the adaptive gain control algorithm during a postprocessing procedure, the input unit array 308 may be permitted to collect information regarding a wide range of sounds caused by the heart, lungs, etc. Because the input units 302a-n in the input unit array 308 can be placed in different anatomical positions along the surface of the body (or on an entirely different body), different biometric characteristics (e.g., respiratory rate, heart rate, or degree of wheezing, crackling, etc.) can be simultaneously monitored by the electronic stethoscope system 300.

Figure 4:
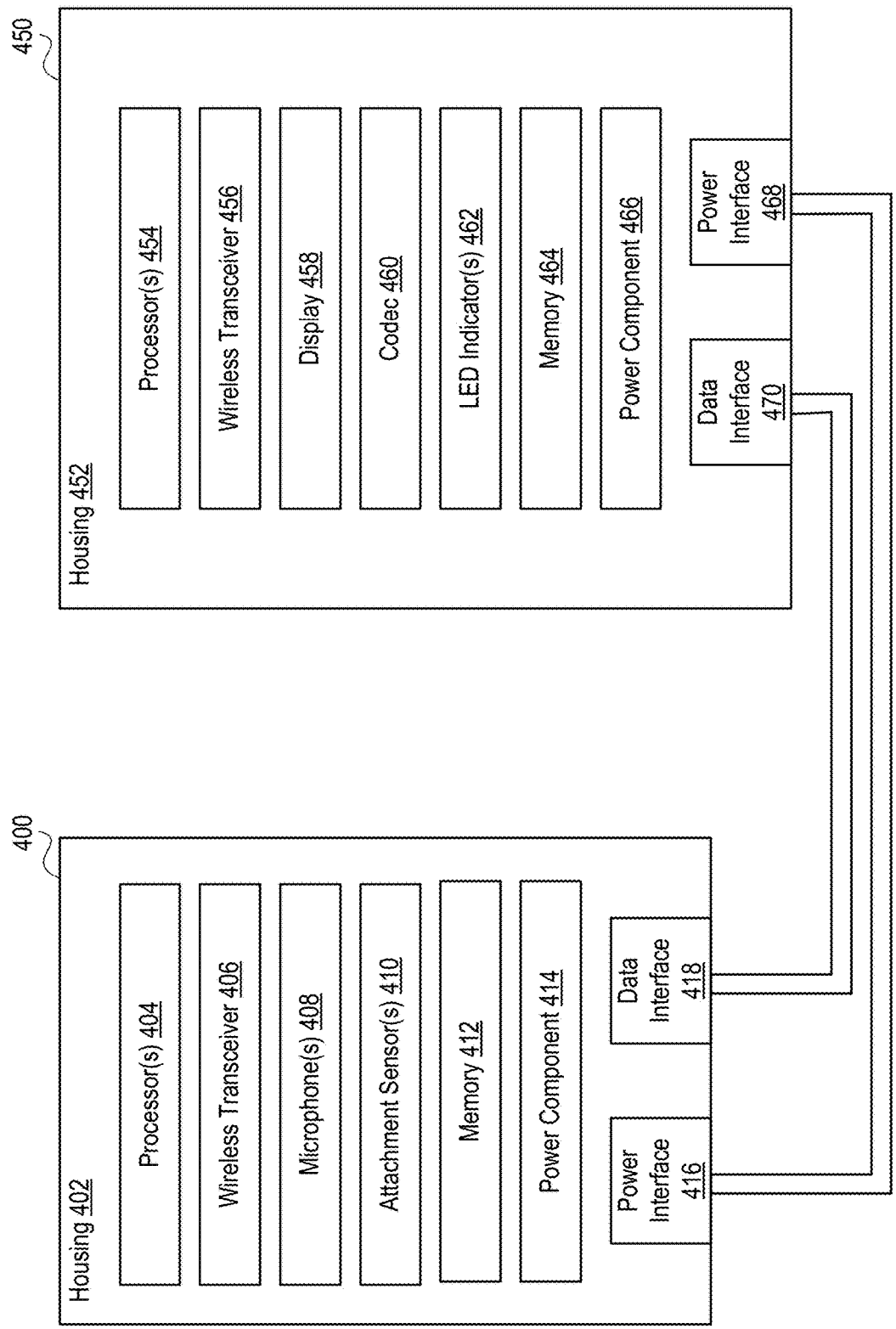
FIG. 4 is a high-level block diagram illustrating exemplary components of an input unit and a hub unit of an electronic stethoscope system.

FIG. 4 is a high-level block diagram illustrating exemplary components of an input unit 400 and a hub unit 450 of an electronic stethoscope system. Embodiments of the input unit 400 and the hub unit 450 can include any subset of the components shown in FIG. 4, as well as additional components not illustrated here. For example, the input unit 400 may include a biometric sensor capable of monitoring a biometric characteristic of the body, such as perspiration (e.g., based on skin humidity), temperature, etc. Additionally or alternatively, the biometric sensor may be designed to monitor a breathing pattern (also referred to as a "respiratory pattern"), record electrical activity of the heart, etc. As another example, the input unit 400 may include an inertial measurement unit (IMU) capable of generating data from which gesture, orientation, or position can be derived. An IMU is an electronic component designed to measure the force, angular rate, inclination, and/or magnetic field of an object. Generally, IM Us include accelerometer(s), gyroscope(s), magnetometer(s), or any combination thereof.

The input unit 400 can include one or more processors 404, a wireless transceiver 406, one or more microphones 408, one or more attachment sensors 410, a memory 412, and/or a power component 414 that is electrically coupled to a power interface 416. These components may reside within a housing 402 (also referred to as a "structural body").

As noted above, the microphone(s) 408 can convert acoustic sound waves into an electrical signal. The microphone(s) 408 may include auscultation microphone(s) configured to produce audio data indicative of internal sounds, ambient microphone(s) configured to produce audio data indicative of ambient sounds, or any combination thereof. Audio data representative of values of the electrical signal can be stored, at least temporarily, in the memory 412. In some embodiments, the processor(s) 404 process the audio data prior to transmission downstream to the hub unit 450. For example, the processor(s) 404 may apply algorithms designed for digital signal processing, denoising, gain control, noise cancellation, artifact removal, feature identification, etc. In other embodiments, minimal processing is performed by the processor(s) 404 prior to transmission downstream to the hub unit 450. For example, the processor(s) 404 may simply append metadata to the audio data that specifies the identity of the input unit 400 or examine metadata already added to the audio data by the microphone(s) 408.

In some embodiments, the input unit 400 and the hub unit 450 transmit data between one another via a cable connected between corresponding data interfaces 418, 470. For example, audio data generated by the microphone(s) 408 may be forwarded to the data interface 418 of the input unit 400 for transmission to the data interface 470 of the hub unit 450. Alternatively, the data interface 470 may be part of the wireless transceiver 456. The wireless transceiver 406 could be configured to automatically establish a wireless connection with the wireless transceiver 456 of the hub unit 450. The wireless transceivers 406, 456 may communicate with one another via a bidirectional communication protocol, such as Near Field Communication (NFC), wireless USB, Bluetooth®, Wi-Fi®, a cellular data protocol (e.g., LTE, 3G, 4G, or 5G), or a proprietary point-to-point protocol.

The input unit 400 may include a power component 414 able to provide power to the other components residing within the housing 402, as necessary. Similarly, the hub unit 450 can include a power component 466 able to provide power to the other components residing within the housing 452. Examples of power components include rechargeable lithium-ion (Li-Ion) batteries, rechargeable nickel-metal hydride (NiMH) batteries, rechargeable nickel-cadmium (NiCad) batteries, etc. In some embodiments, the input unit 400 does not include a dedicated power component, and thus must receive power from the hub unit 450. A cable designed to facilitate the transmission of power (e.g., via a physical connection of electrical contacts) may be connected between a power interface 416 of the input unit 400 and a power interface 468 of the hub unit 450.

The power channel (i.e., the channel between power interface 416 and power interface 468) and the data channel (i.e., the channel between data interface 418 and data interface 470) have been shown as separate channels for the purpose of illustration only. Those skilled in the art will recognize that these channels could be included in the same cable. Thus, a single cable capable of carrying data and power may be coupled between the input unit 400 and the hub unit 450.

The hub unit 450 can include one or more processors 454, a wireless transceiver 456, a display 458, a codec 460, one or more light-emitting diode (LED) indicators 462, a memory 464, and a power component 466. These components may reside within a housing 452 (also referred to as a "structural body"). As noted above, embodiments of the hub unit 450 may include any subset of these components, as well as additional components not shown here.

As shown in FIG. 4, embodiments of the hub unit 450 may include a display 458 for presenting information such as the respiratory status or heart rate of an individual under examination, a network connectivity status, a power connectivity status, a connectivity status for the input unit 400, etc. The display 458 may be controlled via tactile input mechanisms (e.g., buttons accessible along the surface of the housing 452), audio input mechanisms (e.g., microphones), and the like. As another example, some embodiments of the hub unit 450 include LED indicator(s) 462 for operation guidance rather than the display 458. In such embodiments, the LED indicator(s) 462 may convey information similar to that presented by the display 458. As another example, some embodiments of the hub unit 450 include a display 458 and LED indicator(s) 462.

Upon receiving audio data representative of the electrical signal generated by the microphone(s) 408 of the input unit 400, the hub unit 450 may provide the audio data to a codec 460 that is responsible for decoding the incoming data. The codec 460 may, for example, decode the audio data (e.g., by reversing encoding applied by the input unit 400) in preparation for editing, processing, etc. The codec 460 may be designed to sequentially or simultaneously process audio data generated by the auscultation microphone(s) in the input unit 400 and audio data generated by the ambient microphone(s) in the input unit 400.

Thereafter, the processor(s) 454 can process the audio data. Much like the processor(s) 404 of the input unit 400, the processor(s) 454 of the hub unit 450 may apply algorithms designed for digital signal processing, denoising, gain control, noise cancellation, artifact removal, feature identification, etc. Some of these algorithms may not be necessary if already applied by the processor(s) 404 of the input unit 400. For example, in some embodiments the processor(s) 454 of the hub unit 450 apply algorithm(s) to discover diagnostically relevant features in the audio data, while in other embodiments such action may not be necessary if the processor(s) 404 of the input unit 400 have already discovered the diagnostically relevant features. Alternatively, the hub unit 450 may forward the audio data to a destination (e.g., a diagnostic platform running on a computing device or decentralized system) for analysis, as further discussed below. Generally, a diagnostically relevant feature will correspond to a pattern of values in the audio data matching a predetermined pattern-defining parameter. As another example, in some embodiments the processor(s) 454 of the hub unit 450 apply algorithms to reduce noise in the audio data to improve the signal-to-noise (SNR) ratio, while in other embodiments these algorithms are applied by the processor(s) 404 of the input unit 400.

In addition to the power interface 468, the hub unit 450 may include a power port. The power port (also referred to as a "power jack") enables the hub unit 450 to be physically connected to a power source (e.g., an electrical outlet). The power port may be capable of interfacing with different connector types (e.g., C13, C15, C19). Additionally or alternatively, the hub unit 450 may include a power receiver that has an integrated circuit (also referred to as a "chip") able to wirelessly receive power from an external source. Similarly, the input unit 400 may include a power receiver that has a chip able to wirelessly receive power from an external source, for example, if the input unit 400 and hub unit 450 are not physically connected to one another via a cable. The power receiver may be configured to receive power transmitted in accordance with the Qi standard developed by the Wireless Power Consortium or some other wireless power standard.

In some embodiments, the housing 452 of the hub unit 450 includes an audio port. The audio port (also referred to as an "audio jack") is a receptacle that can be used to transmit signals, such as audio, to an appropriate plug of an attachment, such as headphones. An audio port typically includes one, two, three, or four contacts that enable audio signals to be readily transmitted when an appropriate plug is inserted into the audio port. For example, most headphones include a plug designed for a 3.5-millimeter (mm) audio port. Additionally or alternatively, the wireless transceiver 456 of the hub unit 450 may be able to transmit audio signals directly to wireless headphones (e.g., via NFC, Wireless USB, Bluetooth, etc.).

As noted above, the processor(s) 404 of the input unit 400 and/or the processor(s) 454 of the hub unit 450 can apply a variety of algorithms to support different functionalities. Examples of such functionalities include attenuation of lost data packets in the audio data, noise-dependent volume control, dynamic range compression, automatic gain control, equalization, noise suppression, and acoustic echo cancellation. Each functionality may correspond to a separate module residing in a memory (e.g., memory 412 of the input unit 400 or memory 464 of the hub unit 450). Thus, the input unit 400 and/or the hub unit 450 may include an attenuation module, a volume control module, a compression module, a gain control module, an equalization module, a noise suppression module, an echo cancellation module, or any combination thereof.

Note that, in some embodiments, the input unit 400 is configured to transmit audio data generated by the microphone(s) 408 directly to a destination other than the hub unit 450. For example, the input unit 400 may forward the audio data to the wireless transceiver 406 for transmission to a diagnostic platform that is responsible for analyzing the audio data. The audio data may be transmitted to the diagnostic platform instead of, or in addition to, the hub unit 450. If the audio data is forwarded to the diagnostic platform in addition to the hub unit 450, then the input unit 400 may generate a duplicate copy of the audio data and then forward those separate copies onward (e.g., to the wireless transceiver 406 for transmission to the diagnostic platform, to the data interface 418 for transmission to the hub unit 450). As further discussed below, the diagnostic platform normally resides on a computing device that is communicatively connected to the input unit 400, though aspects of the diagnostic platform could reside on the input unit 400 or hub unit 450.

Additional information on electronic stethoscope systems can be found in U.S. Pat. No. 10,555,717, which is incorporated by reference herein in its entirety.

Overview of Diagnostic Platform

Figure 5:
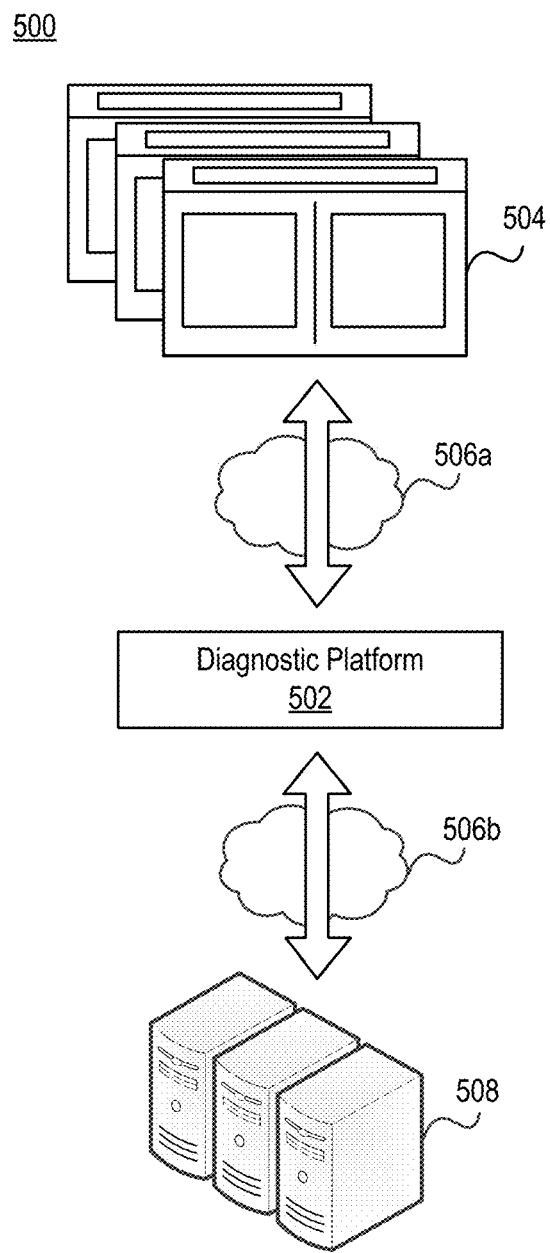
FIG. 5 illustrates a network environment that includes a diagnostic platform.

FIG. 5 illustrates a network environment 500 that includes a diagnostic platform 502. Individuals can interact with the diagnostic platform 502 via interfaces 504. For example, patients may be able to access interfaces through which information regarding audio data, diseases, treatments, and feedback can be provided. As another example, healthcare professionals may be able to access interfaces through which audio data and analyses of the audio data can be reviewed for the purpose of determining an appropriate diagnosis, monitoring health, etc. At a high level, the interfaces 504 may be intended to serve as informative dashboards for either patients or healthcare professionals.

As shown in FIG. 5, the diagnostic platform 502 may reside in a network environment 500. Thus, the diagnostic platform 502 may be connected to one or more networks 506a-b. The network(s) 506a-b can include personal area networks (PANs), local area networks (LANs), wide area networks (WANs), metropolitan area networks (MANs), cellular networks, the Internet, etc. Additionally or alternatively, the diagnostic platform 502 can be communicatively coupled to one or more computing devices over a short-range wireless connectivity technology, such as Bluetooth, NFC, Wi-Fi Direct (also referred to as "Wi-Fi P2P"), and the like.

The interfaces 504 may be accessible via a web browser, desktop application, mobile application, or over-the-top (OTT) application. For example, a healthcare professional may be able to access an interface through which information regarding a patient can be input. Such information can include name, date of birth, diagnoses, symptoms, or medications. Alternatively, the information may be automatically populated into the interface by the diagnostic platform 502 (e.g., based on data stored in a network-accessible server system 508), though the healthcare professional may be permitted to adjust the information as necessary. As further discussed below, the healthcare professional may also be able to access an interface on which audio data and analyses of the audio data can be presented for review. With this information, the healthcare professional may be able to readily establish the status of the patient (e.g., breathing or not breathing), render diagnoses (e.g., based on the presence of wheezing, crackling, etc.), and the like. Accordingly, the interfaces 504 may be viewed on computing devices such as mobile workstations (also referred to as "medical carts"), personal computers, tablet computers, mobile phones, wearable electronic devices, and virtual or augmented reality systems.

In some embodiments, at least some components of the diagnostic platform 502 are hosted locally. That is, part of the diagnostic platform 502 may reside on the computing device used to access one of the interfaces 504. For example, the diagnostic platform 502 may be embodied as a mobile application executing on a mobile phone associated with a healthcare professional. Note, however, that the mobile application may be communicatively connected to a network-accessible server system 508 on which other components of the diagnostic platform 502 are hosted.

In other embodiments, the diagnostic platform 502 is executed entirely by a cloud computing service operated by, for example, Amazon Web Services®, Google Cloud Platform™, or Microsoft Azure®. In such embodiments, the diagnostic platform 502 may reside on a network-accessible server system 508 that comprises one or more computer servers. These computer servers can include models, algorithms (e.g., for processing audio data, calculating respiratory rate, etc.), patient information (e.g., profiles, credentials, and health-related information such as age, date of birth, geographical location, disease classification, disease state, healthcare provider, etc.), and other assets. Those skilled in the art will recognize that this information could also be distributed amongst the network-accessible server system 508 and one or more computing devices or distributed across a decentralized network infrastructure such as a blockchain.

Figure 6:
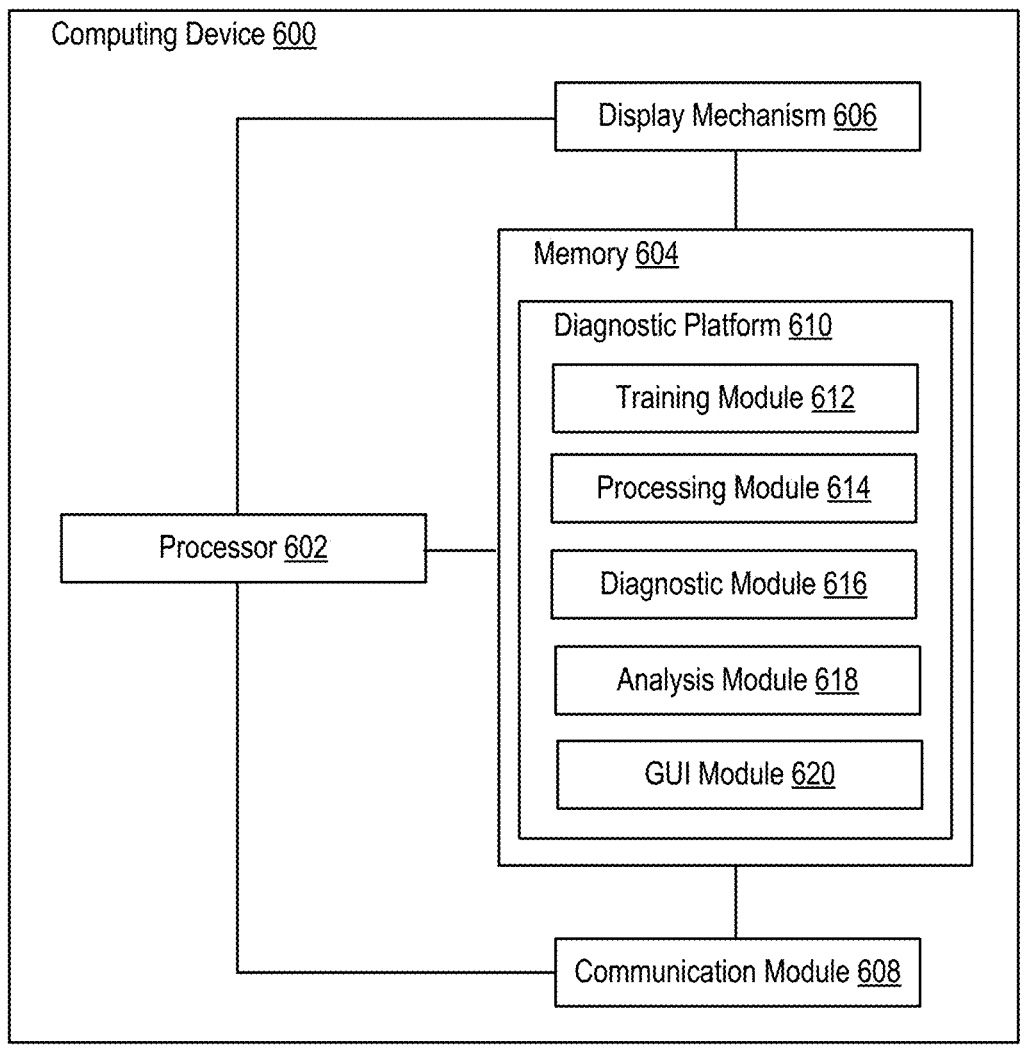
FIG. 6 illustrates an example of a computing device that is able to implement a diagnostic platform designed to produce outputs that are helpful in detecting, diagnosing, and monitoring changes in the health of a patient.

FIG. 6 illustrates an example of a computing device 600 that is able to implement a diagnostic platform 610 designed to produce outputs that are helpful in detecting, diagnosing, and monitoring changes in the health of a patient. As further discussed below, the diagnostic platform 610 can apply a model to audio data associated with a patient in order to identify occurrences of respiratory events (also referred to as "breathing events" or "breaths") and then apply an algorithm to those respiratory events in order to gain insights into the health of the patient. The terms "respiratory event" and "breathing event" may be used to refer to inhalations or exhalations. For example, the algorithm may output a metric that is representative of the respiratory rate as further discussed below. Thus, the diagnostic platform 610 may not only discover patterns of values in the audio data that are diagnostically relevant but may also generate visualizations of those patterns in a manner that is helpful for understanding the present health of the patient. For the purpose of illustration, embodiments may be described in the context of audio data that is generated by an electronic stethoscope system. However, those skilled in the art will recognize that the audio data could be obtained from another source.

Normally, the computing device 600 is associated with a healthcare professional or healthcare facility. For example, the computing device 600 may be a mobile workstation that is situated in an operating room of a hospital, or the computing device 600 may be a mobile phone or tablet computer that is accessible to the healthcare professional while providing services to the patient. Alternatively, the computing device 600 may be the hub unit of the electronic stethoscope system.

The computing device 600 can include a processor 602, memory 604, display mechanism 606, and communication module 608. Each of these components is discussed in greater detail below. Those skilled in the art will recognize that different combinations of these components may be present depending on the nature of the computing device 600.

The processor 602 can have generic characteristics similar to general-purpose processors, or the processor 602 may be an application-specific integrated circuit (ASIC) that provides control functions to the computing device 600. As shown in FIG. 6, the processor 602 can be connected to all components of the computing device 600, either directly or indirectly, for communication purposes.

The memory 604 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 602, the memory 604 can also store data generated by the processor 602 (e.g., when executing the modules of the diagnostic platform 610). Note that the memory 604 is merely an abstract representation of a storage environment. The memory 604 could be comprised of actual memory chips or modules.

The display mechanism 606 can be any component that is operable to visually convey information. For example, the display mechanism 606 may be a panel that includes LEDs, organic LEDs, liquid crystal elements, or electrophoretic elements. In embodiments where the computing device 600 is representative of a hub unit of an electronic stethoscope system, the display mechanism 606 may be a display panel (e.g., display 458 of FIG. 4) or LED indicators (e.g., LED indicators 462 of FIG. 4). In some embodiments, the display mechanism 606 is touch sensitive. Thus, an individual may be able to provide input to the diagnostic platform 610 by interacting with the display mechanism 606. In embodiments where the display mechanism 606 is not touch sensitive, the individual may be able to interact with the diagnostic platform 610 using a control device (not shown), such as a keyboard, physical element (e.g., a mechanical button or knob), or pointing device (e.g., a computer mouse).

The communication module 608 may be responsible for managing communications between the components of the computing device 600, or the communication module 608 may be responsible for managing communications with other computing devices (e.g., the network-accessible server system 508 of FIG. 5). The communication module 608 may be wireless communication circuitry that is designed to establish communication channels with other computing devices. Examples of wireless communication circuitry include antenna modules configured for cellular networks (also referred to as "mobile networks") and chips configured for NFC, Wireless USB, Bluetooth, and the like.

For convenience, the diagnostic platform 610 may be referred to as a computer program that resides in the memory 604 and is executed by the processor 602. However, the diagnostic platform 610 could be comprised of software, firmware, or hardware that is implemented in, or accessible to, the computing device 600. In accordance with embodiments described herein, the diagnostic platform 610 may include a training module 612, processing module 614, diagnostic module 616, analysis module 618, and graphical user interface (GUI) module 620.

The training module 612 may be responsible for training the models that are to be used by the diagnostic platform 610. Training may be done in a supervised, semi-supervised, or unsupervised manner. Assume, for example, that the training module 612 receives input indicative of a request to train a model to identify breathing events in audio data. In such a scenario, the training module 612 may obtain an untrained model and then train the model using audio data that has been labeled, for example, as "breathing event" or "no breathing event." Accordingly, labeled audio data may be provided to the model as training data so that the model learns how to identify breathing events. Normally, the model will learn to identify patterns of values in audio data that are indicative of breathing events.

The processing module 614 can process audio data obtained by the diagnostic platform 610 into a format that is suitable for the other modules. For example, the processing module 614 may apply rules, heuristics, or algorithms to the audio data in preparation for analysis by the diagnostic module 616. As another example, the processing module 614 may apply rules, heuristics, or algorithms to outputs produced by the diagnostic module 616 in preparation for analysis by the analysis module 618. Accordingly, the processing module 614 may be responsible for ensuring that the appropriate data is accessible to the other modules of the diagnostic platform 610. Moreover, the processing module 614 may be responsible for ensuring that outputs produced by the other modules of the diagnostic platform 610 are suitable for storage (e.g., in the memory 604) or transmission (e.g., via the communication module 608).

The diagnostic module 616 may be responsible for identifying the appropriate model to apply to audio data obtained by the diagnostic platform 610. For instance, the diagnostic module 616 may identify the appropriate model based on an attribute of the audio data, the patient, or the electronic stethoscope system. These attributes may be specified in metadata that accompanies the audio data. As an example, the appropriate model may be identified based on the anatomical region for which internal sounds have been recorded. Alternatively, the diagnostic module 616 may identify the appropriate model based on the metrics to be produced by the analysis module 618. As an example, if the analysis module 618 is tasked with computing the respiratory rate, then the diagnostic module 616 may identify a module that is capable of discovering breathing events. The desired metric(s) may be specified by a healthcare professional, or the desired metric(s) may be determined by the diagnostic platform 610.

Generally, the model applied to the audio data by the diagnostic module 616 is one of multiple models maintained in the memory 604. These models may be associated with different breathing events, ailments, and the like. For example, a first model may be designed and then trained to identify inhalations and exhalations, and a second model may be designed and then trained to identify instances of wheezing or crackling.

At a high level, each model may be representative of a collection of algorithms that, when applied to audio data, produce an output that conveys information that may provide insight into the health of the patient. For example, if the model applied by the diagnostic module 616 identifies inhalations and exhalations, then the outputs may be useful in establishing whether the patient is breathing normally or abnormally. As another example, if the model applied by the diagnostic module 616 identifies instances of wheezing or crackling, then the outputs may be useful in establishing whether the patient is suffering from a given disease.

In some scenarios, the outputs produced by the models applied by the diagnostic module 616 are not particularly useful on their own. The analysis module 618 may be responsible for considering the context of these outputs in a more holistic sense. For example, the analysis module 618 may produce one or more metrics that are representative of the health of the patient based on the outputs produced by models applied by the diagnostic module 616. These metrics may provide insight into the health of the patient without requiring full analysis or awareness of the outputs produced by the models. Assume, for example, that the model applied by the diagnostic module 616 identifies breathing events based on an analysis of audio data. While knowledge of the breathing events may be useful, a healthcare professional may be more interested in a metric such as respiratory rate. The analysis module 618 may compute the respiratory rate based on the breathing events identified by the diagnostic module 616.

The GUI module 620 may be responsible for establishing how to present information for review on the display mechanism 606. Various types of information can be presented depending on the nature of the display mechanism 606. For example, information that is derived, inferred, or otherwise obtained by the diagnostic module 616 and analysis module 618 may be presented on an interface for display to a healthcare professional. As another example, visual feedback may be presented on an interface so as to indicate when a patient has experienced a change in health.

Figure 7:
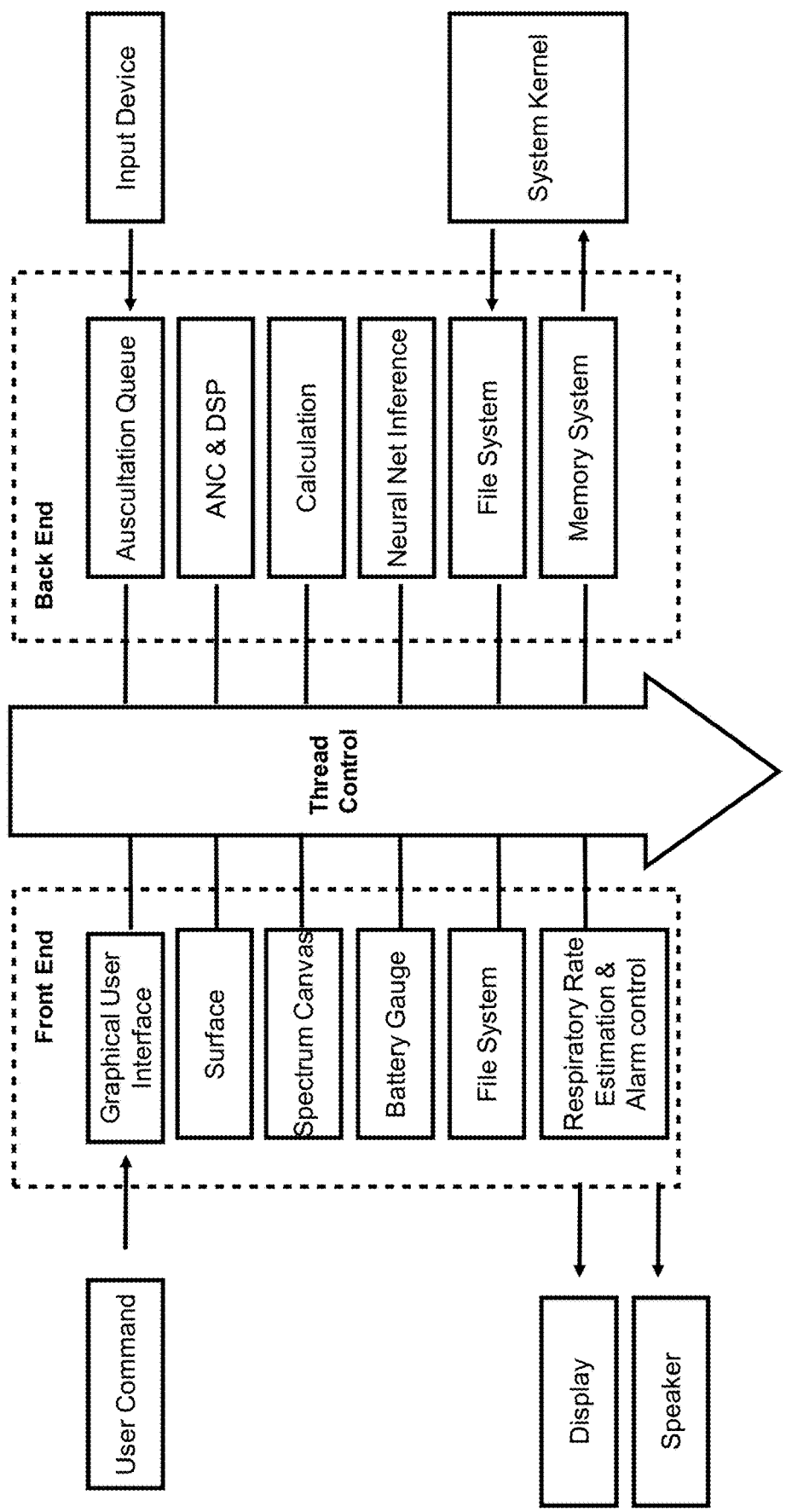
FIG. 7 includes an example of a workflow diagram that illustrates how audio data obtained by a diagnostic platform can be processed by a background service before analyses of the audio data are presented on an interface for review.

FIG. 7 includes an example of a workflow diagram that illustrates how audio data obtained by a diagnostic platform can be processed by a background service before analyses of the audio data are presented on an interface for review. As shown in FIG. 7, data may be obtained and processed by the "back end" of the diagnostic platform, while analyses of that data may be presented by the "front end" of the diagnostic platform. Individuals, such as healthcare professionals and patients, may also be able to interact with the diagnostic platform through its front end. For example, commands may be issued through interfaces shown on a display.

Moreover, the diagnostic platform may be able to generate notifications as further discussed below. For example, if the diagnostic platform determines that the respiratory rate of a patient falls beneath a determined threshold, then the diagnostic platform may generate a notification that serves as an alarm. The notification may be visually presented via a display and/or audibly presented via a speaker.

Approaches to Establishing the Respiratory Rate

Conventional approaches to computing the respiratory rate suffer from several drawbacks.

Some approaches rely on observing inhalations and exhalations over a relatively long interval of time. It is not unusual for this "observation interval" to last 60 seconds or more. Because the observation interval is so long, these approaches cannot account for short-lived events like apnea. As a result, healthcare professionals may be largely, if not entirely, unaware of temporary cessations of breathing since there will be little impact to the respiratory rate across the entire observation interval. Misunderstanding the respiratory rate can lead to significant harm as cessations of breathing may need to be addressed immediately.

Other approaches rely on monitoring movement of the chest or end-tidal carbon dioxide ($CO_2$) in exhaled air. These approaches are not practical or suitable in many situations, however. For example, chest movement may not be an accurate indicator of breathing events—especially if the patient is under general anesthesia or experiencing a medical event (e.g., a seizure), and the composition of exhaled air may not be known if the patient is not wearing a mask.

Introduced here is an approach that addresses these drawbacks by computing the respiratory rate through analysis of audio data. As discussed above, this approach relies on inhalations and exhalations being detected in a consistent, accurate manner. In auscultation, these breathing events are important for diagnostic determination by healthcare professionals.

At a high level, the approach involves two phases, a first phase in which inhalations and exhalations are detected and then a second phase in which these inhalations and exhalations are used to compute the respiratory rate. The first phase may be referred to as the "detection phase," and the second phase may be referred to as the "computation phase."

A. Breathing Event Detection

Figure 8:
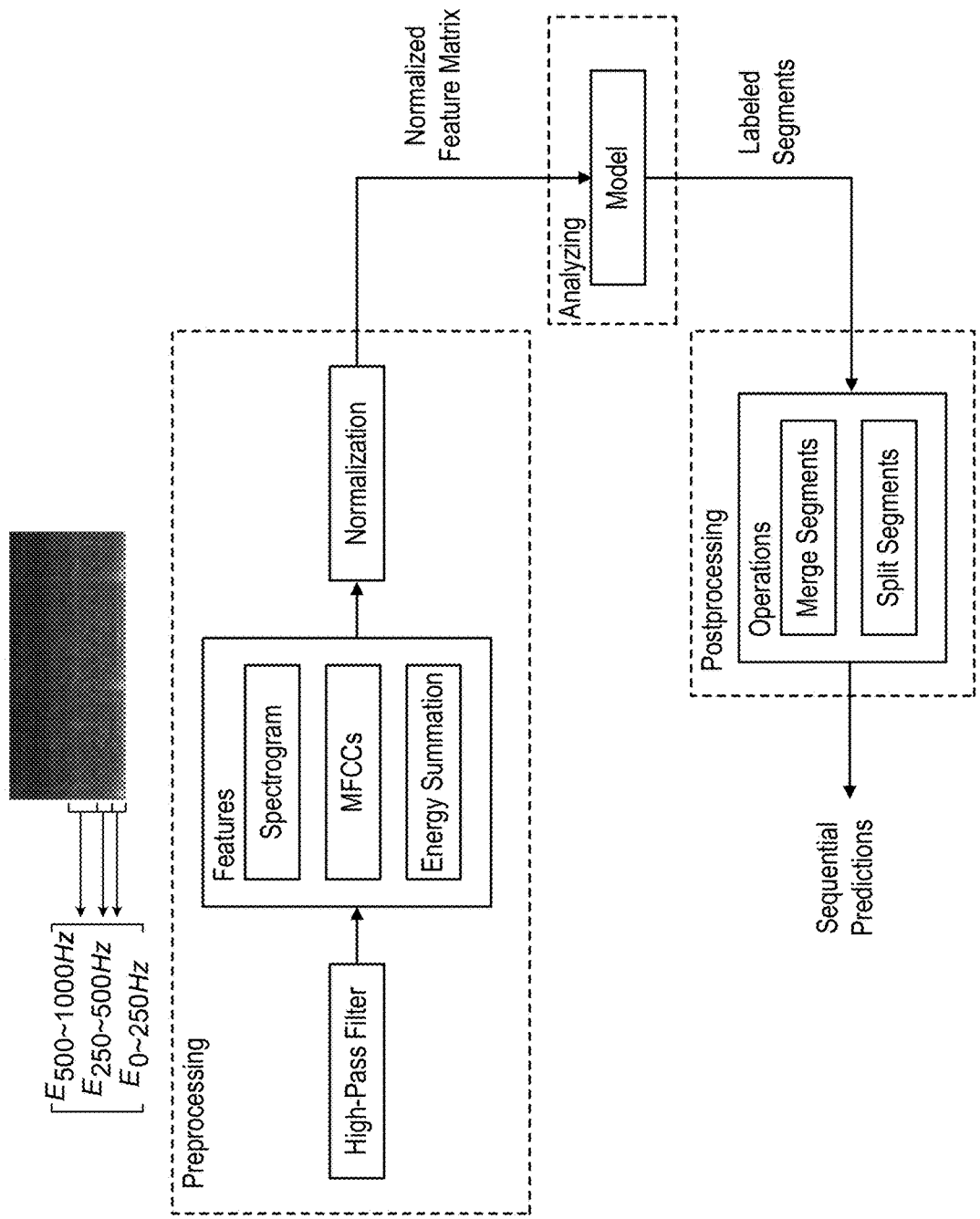
FIG. 8 includes a high-level illustration of a computational pipeline that may be employed by a diagnostic platform during the detection phase.

FIG. 8 includes a high-level illustration of a computational pipeline that may be employed by a diagnostic platform during the detection phase. One advantage of this computational pipeline (also referred to as a "computational framework") is its modular design. Each "unit" can be separately tested and then adjusted in order to achieve the best overall performance. Moreover, the outputs of some units may be used for multiple purposes. For example, the spectrogram produced during preprocessing could be provided to a model as input and/or posted to an interface for real-time review.

For simplicity, this framework is divided into three parts, namely, preprocessing, analyzing, and postprocessing. Preprocessing may comprise not only processing the audio data but also employing feature engineering techniques. Analyzing may comprise employing the model that is trained to identify breathing events. As mentioned above, the model may include a neural network that is designed to produce, as output, a sequence of detections (e.g., of breathing events) rather than a single detection (e.g., a classification or diagnosis). Each detection may be representative of a separate prediction that is made independently by the model. Finally, postprocessing may comprise examining and/or splitting the detections produced by the model. Normally, preprocessing is performed by a processing module (e.g., processing module 614 of FIG. 6), analyzing is performed by a diagnostic module (e.g., diagnostic module 616 of FIG. 6), and postprocessing is performed by an analysis module (e.g., analysis module 618 of FIG. 6).

Further details regarding each part are provided below in the context of an example. Those skilled in the art will recognize that the numbers provided below are intended to be illustrative only. One important aspect of the framework is its flexibility, and thus other numbers may be applicable or appropriate in other scenarios.

I. Preprocessing

In this example, audio data that is representative of a recording of internal sounds made by the lungs was processed with a sampling frequency equivalent to 4 kilohertz (kHz). A high-pass filter was then applied to the audio data with an order of 10 and a cut-off frequency of 80 Hz, which removed electrical interference (~60 Hz) and internal sounds made by the heart (~1-2 Hz) or another internal organ. Thus, the diagnostic platform may apply a high-pass filter with a cut-off frequency that is sufficient to filter sounds made by another internal organ that is not of interest. The filtered audio data was then processed using a Short-Time Fourier Transform (STFT). In this example, the STFT had a Hamming window with a window size of 256 and an overlap ratio of 0.25. Thus, a signal of approximately 15 seconds could be transformed into a corresponding spectrogram with a size of 938×129. To exploit the spectral information of the internal sounds of interest, the diagnostic platform extracted (i) a spectrogram, (ii) Mel frequency cepstral coefficients (MFCCs), and (iii) energy summations. In this example, the spectrogram was a 129-bin log magnitude spectrogram. For the MFCCs, the diagnostic platform extracted 20 static coefficients, 20 delta coefficients, and 20 acceleration coefficients. To do this, the diagnostic platform used 40 Mel-bands within the frequency range of 0-4,000 Hz. The width used to calculate the delta and acceleration coefficients was 9 frames. This results in a 60-bin vector per frame. Meanwhile, the diagnostic platform computed the energy summation of three different frequency bands, 0-250 Hz, 251-500 Hz, and 501-1,000 Hz, which results in three values for each frame.

After extracting these features, the diagnostic platform concatenated these features together to form a 938×193 feature matrix. Then, the diagnostic platform applied min-max normalization to each feature so that the normalized features ranged in value between 0 and 1.

II. Analyzing

As mentioned above, the features extracted during preprocessing were provided, as input, to several models that were trained to identify breathing events. To establish the optimal model, six models were tested using the same extracted features. These models included a unidirectional recurrent neural network (Uni-RNN), unidirectional long short-term memory neural network (uni-LSTM), unidirectional gated recurrent unit neural network (Uni-GRU), bidirectional recurrent neural network (Bi-RNN), bidirectional long short-term memory neural network (Bi-LSTM), and bidirectional gated recurrent unit neural network (Bi-GRU). Collectively, these models are referred to as the "baseline models."

Figure 9:
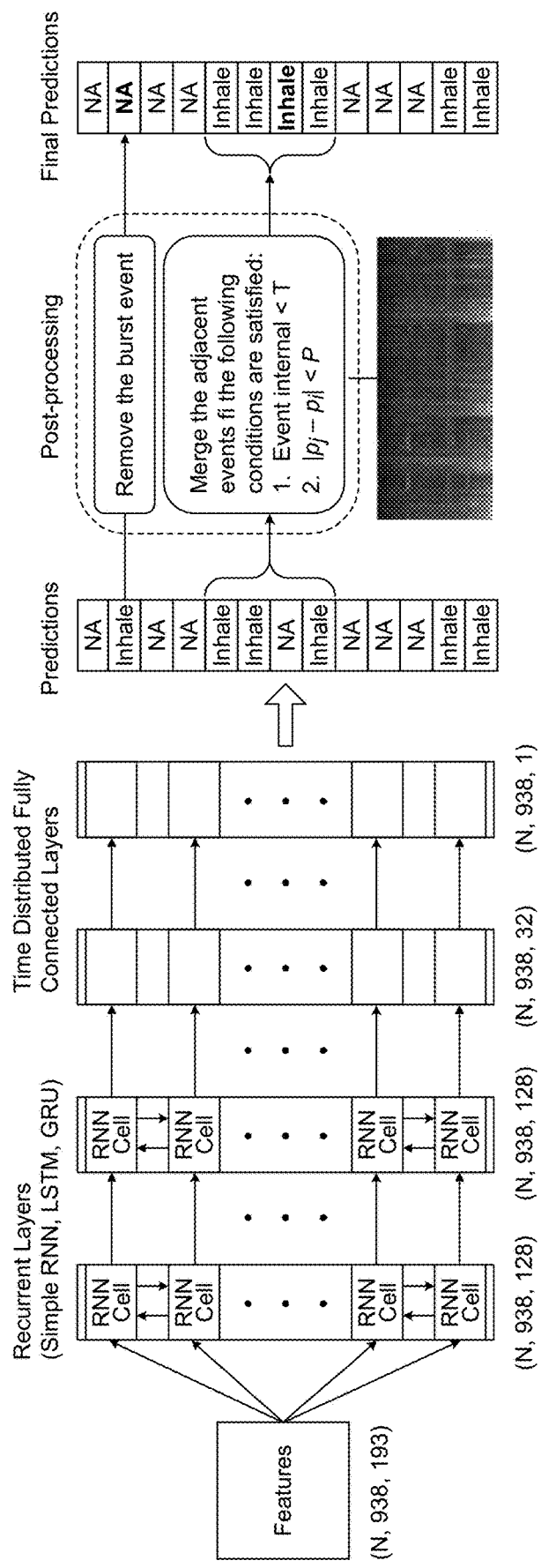
FIG. 9 illustrates the architecture of several baseline models that can be employed by a diagnostic platform.

The architecture of these baseline models is shown in FIG. 9. The baseline models were designed to be capable of detecting breathing events based on an analysis of audio data. The first and second layers are recurrent layers that can be RNN, LSTM, or GRU. These recurrent layers handle the temporal information in the features. Because respiration is usually periodic, these recurrent layers can learn the nature of breath cycles from labeled examples (also referred to as "training data"). In order to detect the start and end times of the breathing events in audio data, the diagnostic platform used a time-distributed fully connected layer as the output layer. This approach resulted in models that are capable of outputting a sequence of detections (e.g., inhale or no action) rather than a single detection. A sigmoid function was used as the activation function in the time-distributed fully connected layer.

Each output produced by each baseline model was a detection vector with a size of 938×1. Each element in this vector was set to 1 to indicate that an inhalation or exhalation existed at the corresponding time segment if the value was above a threshold; otherwise, the value was set to 0. In this example, a single-task learning approach was used for the baseline models, though multi-task learning approaches could also be used.

For the benchmark model, Adaptive Moment Estimation (ADAM) was used as the optimizer. ADAM is a method that computes adaptive learning rates for parameters using stochastic optimization, a process that is important in deep learning and machine learning. The starting learning rate was set to 0.0001 with a step decay (0.2×) when the validation loss did not decrease for 10 epochs. This learning process stopped when there was no improvement for 50 consecutive epochs.

III. Postprocessing

The detection vectors produced by the baseline models can then be further processed for a different purpose. For example, the diagnostic platform may transform each prediction vector from frames to time for use in real-time monitoring by a healthcare professional. Moreover, domain knowledge may be applied as shown in FIG. 9. Because the respiration is known to be performed by a living body, the duration of the breathing event is normally within a certain range. When a detection vector indicates that there are consecutive breathing events (e.g., inhalations) with a small interval therebetween, the diagnostic platform can examine the continuity of these breathing events and then decide whether to merge those breathing events. More specifically, the diagnostic platform can compute the frequency difference of the energy peak ($|p_j-p_i|$) between the j-th and i-th breathing events where the interval between the breathing events is smaller than T seconds. If the difference is smaller than a given threshold P, these breathing events are merged as a single breathing event. In this example, T was set to 0.5 seconds and P was set to 25 Hz. If the breathing event was shorter than 0.05 seconds, then the diagnostic platform can simply delete the breathing event entirely. For example, the diagnostic platform may adjust the label(s) applied to the corresponding segment(s) to indicate that no breathing event occurred.

IV. Task Definition and Evaluation

In this example, two distinct tasks were performed by the diagnostic platform.

Figure 10:
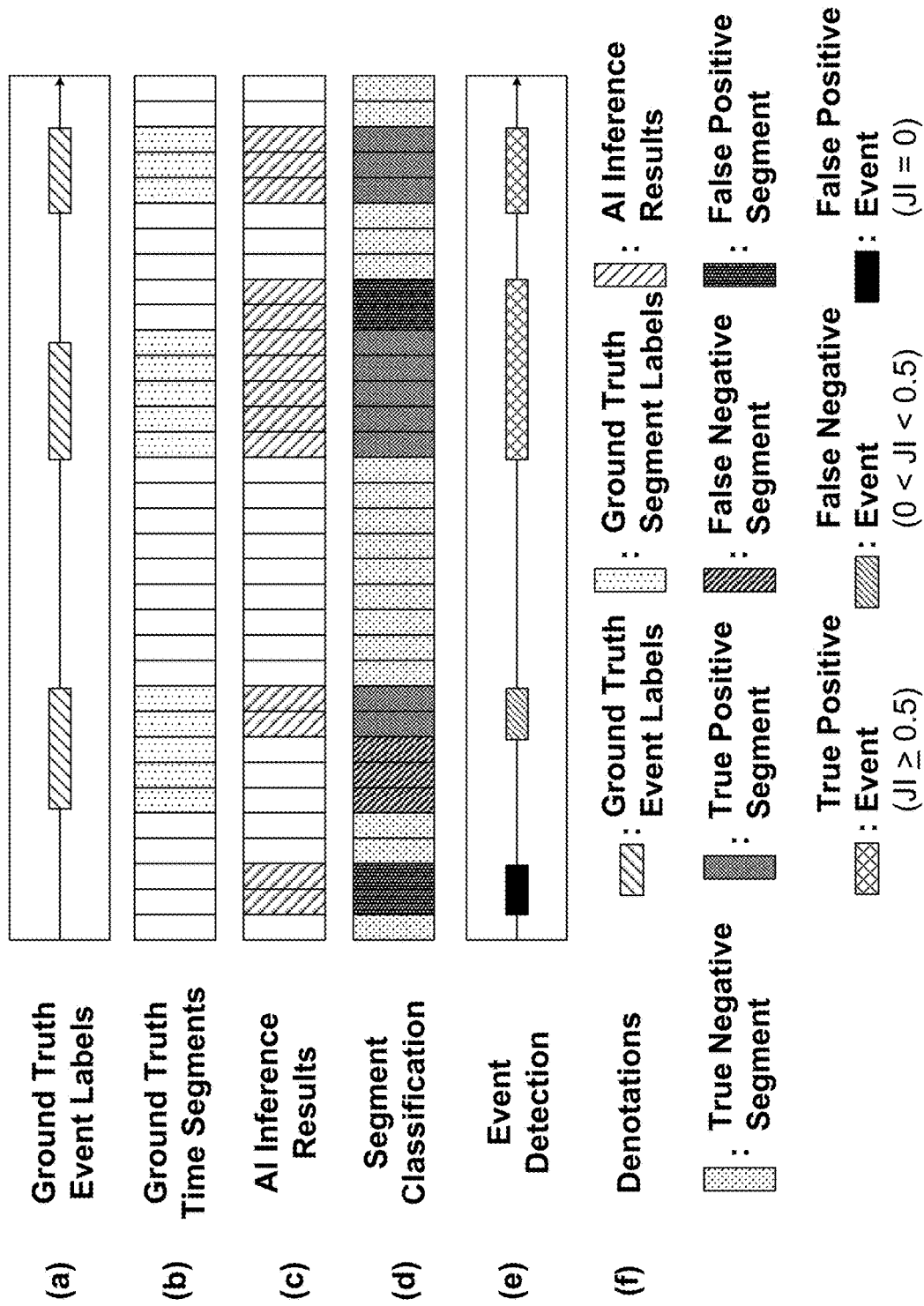
FIG. 10 illustrates how individual segments of audio data can be classified by a diagnostic platform.

The first task was classification of segments of audio data. To accomplish this, a recording of each breathing event was initially transformed to a spectrogram. The temporal resolution of the spectrogram depended on the window size and overlap ratio of the STFT as discussed above. For convenience, these parameters were fixed so that each spectrogram was a matrix with a size of 938×128. Accordingly, each recording was split into 938 segments, and each segment was automatically labeled based on the ground truth labels as shown in FIG. 10.

After a recording undergoes the preprocessing and analyzing, the diagnostic platform will have access to a corresponding output with sequential detections with a size of 938×1. This output may be referred to as the "inference results." By comparing the sequential detections with the ground truth segments, the diagnostic platform is able to define true positives (TP), true negatives (TN), false positives (FP), and false negatives (FN). Then, the sensitivity and specificity of the model used to classify the segments can be computed.

The second task was detection of breathing events in the audio data. After obtaining the sequential detections made by the model, the diagnostic platform can assemble the connected segments with the same label into a corresponding breathing event. For example, the diagnostic platform may specify that connected segments correspond to an inhalation, an exhalation, or no action. Moreover, the diagnostic platform can derive the start and end times of each assembled breathing event. In this example, the Jaccard Index (JI) was used to determine whether one breathing event predicted by the model correctly matched the ground truth event. If the value of the JI exceeded 0.5, the diagnostic platform designated the assembled breathing event as a TP event. If the value of the JI exceeded 0 but fell beneath 0.5, the diagnostic platform designated the assembled breathing event as an FN event. If the value of the JI was 0, the diagnostic platform designated the assembled breathing event as an FP event.

To evaluate performance, the diagnostic platform examined accuracy, sensitivity, positive predictive value, and F1-score of each baseline model. All of the bidirectional models were superior to the unidirectional models. This outcome is largely attributable to the growing complexity (and number of trainable parameters) of the bidirectional models. Overall, Bi-GRU showed the most promise of the baseline models, though there may be situations where the other baseline models are more suitable than Bi-GRU.

B. Respiratory Rate Calculation

Reliable estimation of the respiratory rate plays an important role in the early detection of various illnesses. Abnormal respiratory rates can be suggestive of different diseases, as well as other pathological or psychogenic causes. The search for a clinically acceptable and accurate technique for continuously establishing the respiratory rate has proven to be elusive. Several approaches have been developed in an attempt to fill this clinical gap as discussed above, but none has gained sufficient confidence from healthcare professionals to become a standard of care.

Figure 11A:
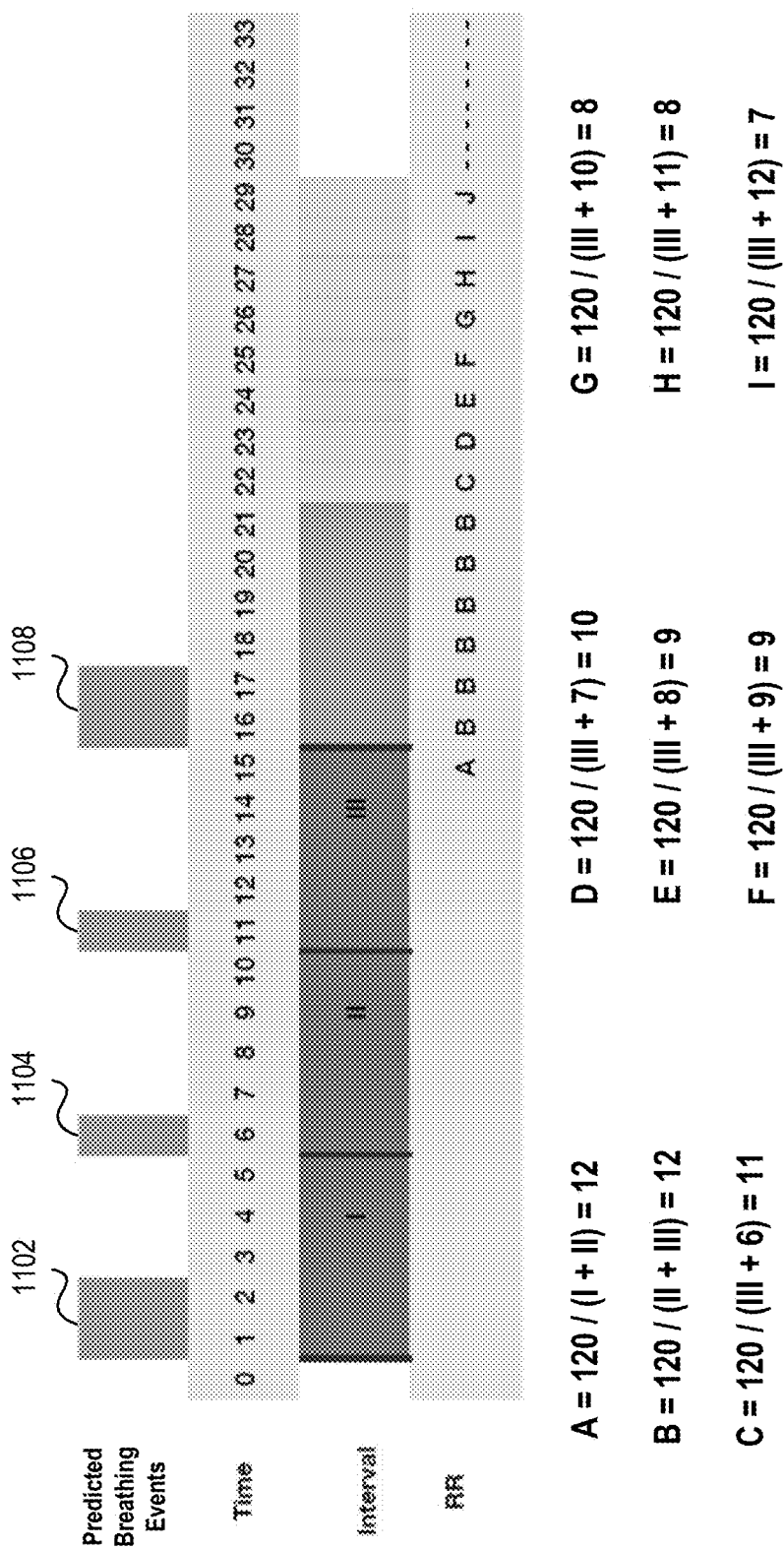
FIG. 11A includes a high-level illustration of an algorithmic approach to estimating the respiratory rate.

FIG. 11A includes a high-level illustration of an algorithmic approach to estimating the respiratory rate. As shown in FIG. 11A, this algorithmic approach relies on breathing events that are predicted by a model employed by the diagnostic platform. Properly identifying breathing events is key to estimating the respiratory rate, so the detecting and computing phases must be consistently completed with high accuracy. Moreover, the detecting and computing phases may be continually performed so that the respiratory rate is estimated in near real time (e.g., every few seconds rather than every 30-60 seconds).

At a high level, this algorithmic approach relies on tracking occurrences of breathing events and then calculating the respiratory rate on an ongoing basis using a sliding window. Initially, the algorithm executed by the diagnostic platform defines a starting point for a window that contains a portion of the audio data obtained for analysis. Then, the diagnostic platform can monitor the breathing events inferred by the model as discussed above in order to define the ending point for the window. The starting and ending points for the window may be defined so that a predetermined number of breathing events are contained within its bounds. Here, for example, the window includes three breathing events, though greater or fewer than three breathing events could be included in the window in other embodiments. In embodiments where the window is programmed to include three breathing events, the starting point for the window corresponds to the beginning of the first breathing event 1102 included in the window, and the ending point for the window corresponds to the beginning of the fourth breathing event 1108. While the fourth breathing event 1108 defines the ending point for the window, the fourth breathing event 1108 is not initially included in the window.

As shown in FIG. 11A, the diagnostic platform can compute the respiratory rate based on the spacing between the inhalations included in the window. Here, the window includes a first breathing event 1102, a second breathing event 1104, and a third breathing event 1106. As mentioned above, a fourth breathing event 1108 may be used to define the ending point for the window. A first period represented by "I" is defined by the interval of time between the beginning of the first breathing event 1102 and the beginning of the second breathing event 1104. A second period represented by "II" is defined by the interval of time between the beginning of the second breathing event 1104 and the beginning of the third breathing event 1106. A third period represented by "III" is defined by the interval of time between the beginning of the third breathing event 1106 and the beginning of the fourth breathing event 1108.

Each period corresponds to a number of frames (and thus an interval of time). Assume, for example, that the audio data obtained by the diagnostic platform is recording that has a total duration of 15 seconds, and that during processing, the recording is split into 938 segments, each of which has a duration of approximately 0.016 seconds. The term "segment" may be used interchangeably with the term "frame." Here, the first, second, and third periods are approximately 5 seconds in length, though the first, second, and third breathing events 1102, 1104, 1106 are different lengths in terms of segments and seconds. Those skilled in the art will recognize, however, that the periods between breathing events need not be identical to one another.

As shown in FIG. 11A, the respiratory rate can be computed on a per-frame basis based on these periods. As an example, consider the fifteenth second represented by "A." At this point, the third period has not yet been defined since the third breathing event 1106 has not yet started. The respiratory rate can be computed by dividing 120 by the sum of the first and second periods in terms of seconds. Beginning at the sixteenth second represented by "B," the diagnostic platform is aware of the third breathing event 1106. Thus, beginning at the sixteenth second, the respiratory rate can be computed by dividing 120 by the sum of the second and third periods in terms of seconds.

Normally, the diagnostic platform calculates the respiratory rate in an ongoing manner as additional breathing events are identified. Said another way, the respiratory rate can be calculated in a "rolling" manner as new periods are identified. Whenever a breathing event is identified (and thus a new period is defined), the diagnostic platform may use the most recent periods to compute the respiratory rate. As an example, assume that the first and second periods correspond to 5 and 7 seconds, respectively. In this scenario, the respiratory rate will be 10 breaths per minute (i.e. 120/I+II=120/5+7). As another example, assume that the first and second periods correspond to 4 and 4 seconds, respectively. In this scenario, the respiratory rate will be 15 breaths per minute (i.e. 120/I+II=120/4+4). After another period (i.e. a third period) has been identified, the respiratory rate can be calculated using the second and third periods rather than the first and second periods.

As mentioned above, because the respiration is known to be performed by a living body, the duration of the breathing event is normally within a certain range. Accordingly, the algorithm employed by the diagnostic platform to calculate the respiratory rate may be programmed to increment the denominator if a new breathing event is not inferred within a certain number of frames or seconds. In FIG. 11A, the algorithm is programmed to increment the denominator responsive to a determination that a new breathing event has not been discovered within 6 seconds. Accordingly, at the twenty-second second represented by "C," the diagnostic platform may calculate the respiratory rate by dividing 120 by the sum of the second period plus 6. Meanwhile, at the twenty-third second represented by "D," the diagnostic platform may calculate the respiratory rate by dividing 120 by the sum of the second period plus 7. As shown in FIG. 11A, the diagnostic platform can continue incrementing the denominator for each second that passes until a new breathing event is discovered.

Such an approach ensures that the respiratory rate is updated in near real time to reflect changes in the health of the patient. If the patient stops breathing entirely, the respiratory rate calculated by the diagnostic platform may not immediately have a value of zero, but the respiratory rate will show a downward trend almost instantaneously that can serve as an alert for healthcare professionals.

To address scenarios where the respiratory rate calculated by the diagnostic platform is abnormally low or high, the algorithm may be programmed with a first threshold (also referred to as a "lower threshold") and a second threshold (also referred to as an "upper threshold"). If the respiratory rate falls beneath the lower threshold, then the algorithm may indicate that a warning should be presented by the diagnostic platform. Moreover, if the diagnostic platform determines that the respiratory rate falls beneath the lower threshold, the diagnostic platform may act as though the respiratory rate is actually zero. Such an approach ensures that the diagnostic platform can readily react to scenarios where no breathing events have been discovered for an extended interval of time without requiring that the respiratory rate actually reach zero. Similarly, if the respiratory rate exceeds the upper threshold, then the algorithm may indicate that a warning should be presented by the diagnostic platform. The lower and upper thresholds may be adjusted—either manually or automatically—based on the patient, the services being provided to the patient, etc. For example, the lower and upper thresholds may be 4 and 60, respectively, for pediatric patients, and the lower and upper thresholds may be 4 and 35, respectively, for adult patients.

For simplicity, the respiratory rate posted for review (e.g., to the interfaces shown in FIGS. 13A-B) may be an integer value, though the respiratory rate may be computed to the first or second decimal place (i.e., to the tenths or hundredths place). This may be helpful in avoiding confusion by healthcare professionals and patients, particularly in urgent situations. As mentioned above, the respiratory rate posted for review may be visually altered in the event that it falls below the lower threshold or exceeds the upper threshold. For example, if the respiratory rate falls below the lower threshold, the diagnostic platform may post a placeholder element (e.g., "–" or "--") that is meant to indicate the respiratory rate is undetectable. If the respiratory rate exceeds the upper threshold, the diagnostic platform may post another placeholder element (e.g., "35+" or "45+") that is meant to indicate the respiratory rate is abnormally high. In many situations, healthcare professionals are more interested in knowing when the respiratory rate is abnormally high than what the exact respiratory rate is exactly.

Generally, the diagnostic platform processes a stream of audio data that is obtained in near real time as recording occurs. Said another way, the diagnostic platform may continually calculate the respiratory rate as new breathing events are discovered as discussed above. However, in some embodiments, the diagnostic platform does not compute the respiratory rate for every single frame in an effort to conserve processing resources. Instead, the diagnostic platform may compute the respiratory rate on a periodic basis, though the respiratory rate will normally still be calculated frequently (e.g., every several seconds) to ensure that healthcare professionals are made aware of any changes in the health of the patient.

Figure 11B:
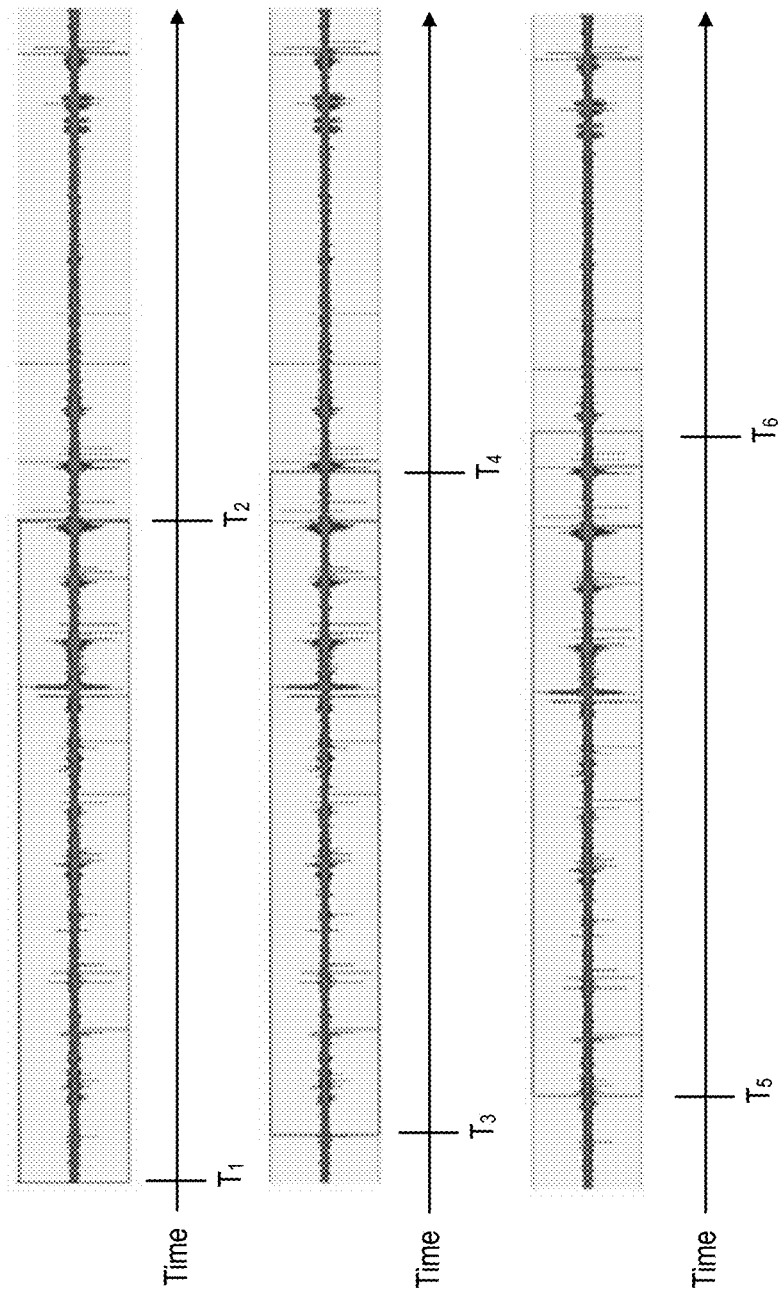
FIG. 11B illustrates how the diagnostic platform may calculate the respiratory rate using a sliding window over a recording of predetermined length that is updated at a predetermined frequency.

FIG. 11B illustrates how the diagnostic platform may calculate the respiratory rate using a sliding window over a recording of predetermined length (e.g., 12, 15, or 20 seconds) that is updated at a predetermined frequency (e.g., every 2, 3, or 5 seconds). In FIG. 11B, the bounding box represents the bounds of the sliding window in which the audio data is processed. After a predetermined amount of time has elapsed, the bounds of the sliding window shift. Here, for example, the sliding window covers 15 seconds and is shifted by 3 seconds, thereby retaining 12 seconds of the audio data contained in the sliding window previously. Such an approach allows the respiratory rate to be computed frequently (e.g., every time the bounds of the sliding window are shifted) without overconsuming available processing resources.

Another approach to computing the respiratory rate relies on autocorrelation rather than ML or AI to perform auscultation. At a high level, the term "autocorrelation" refers to a process in which a signal is correlated with a delayed copy of the signal as a function of delay. Analysis of autocorrelation is a common mathematical tool for identifying repeating patterns, and thus is often used in digital signal processing to derive or infer information regarding repeating events.

Figure 12:
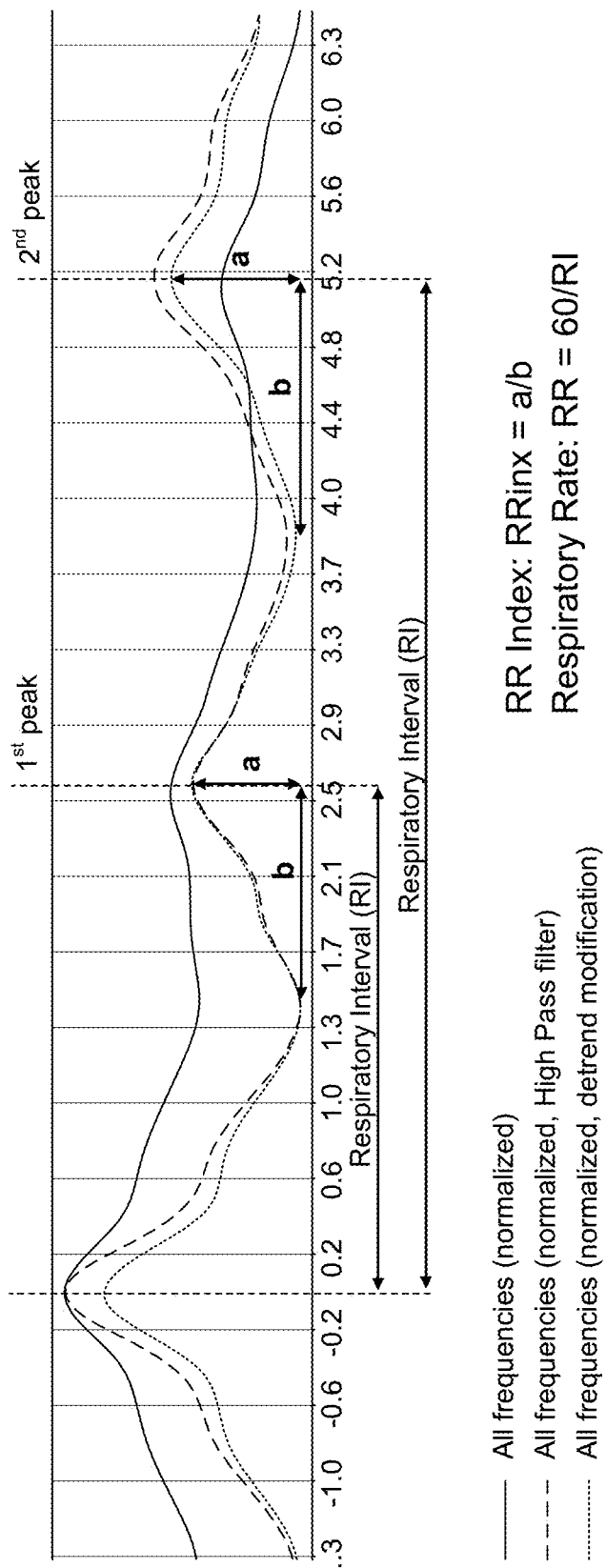
FIG. 12 illustrates an alternative approach to auscultation in which the diagnostic platform uses autocorrelation to identify inhalations and exhalations.

In embodiments where the diagnostic platform uses autocorrelation for detection, the diagnostic platform uses a STFT to convert a recording of audio data into a spectrogram as discussed above. Autocorrelation coefficients are then calculated and plotted for the recording to determine the interval between the inhalations and exhalations as shown in FIG. 12. First, the diagnostic platform may normalize the autocorrelation coefficients to reduce noise. Then, a high-pass filter may be applied to the autocorrelation coefficients so as to eliminate those falling beneath a threshold (e.g., 15 Hz). Moreover, the diagnostic platform may perform detrend modification to further refine the autocorrelation coefficients.

After processing the autocorrelation coefficients, the diagnostic platform can calculate the respiratory rate by dividing 60 by the respiratory interval (RI) between the first- and second-order peaks. The respiratory rate index may determine which the peaks is chosen, for example, with a high respiratory rate index being preferred. Generally, respiratory rate indexes lower than approximately 0.6 are indicative of unstable respiratory rates, and thus may be discarded by the diagnostic platform.

Figure 13A:
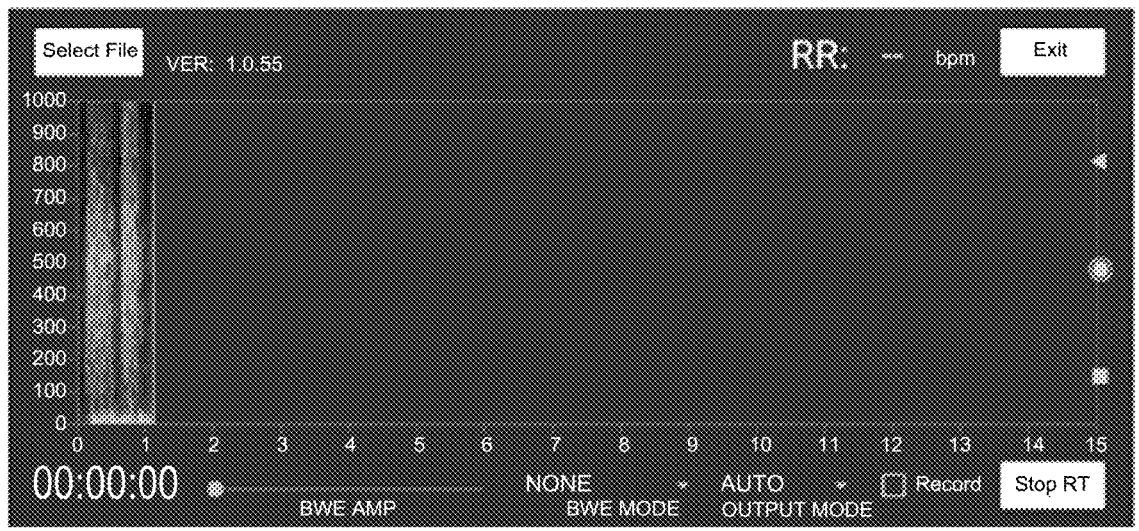
FIG. 13A illustrates how the spectrogram produced by the diagnostic platform may be presented in near real time to facilitate diagnostic determination by a healthcare professional.
Figure 13B:
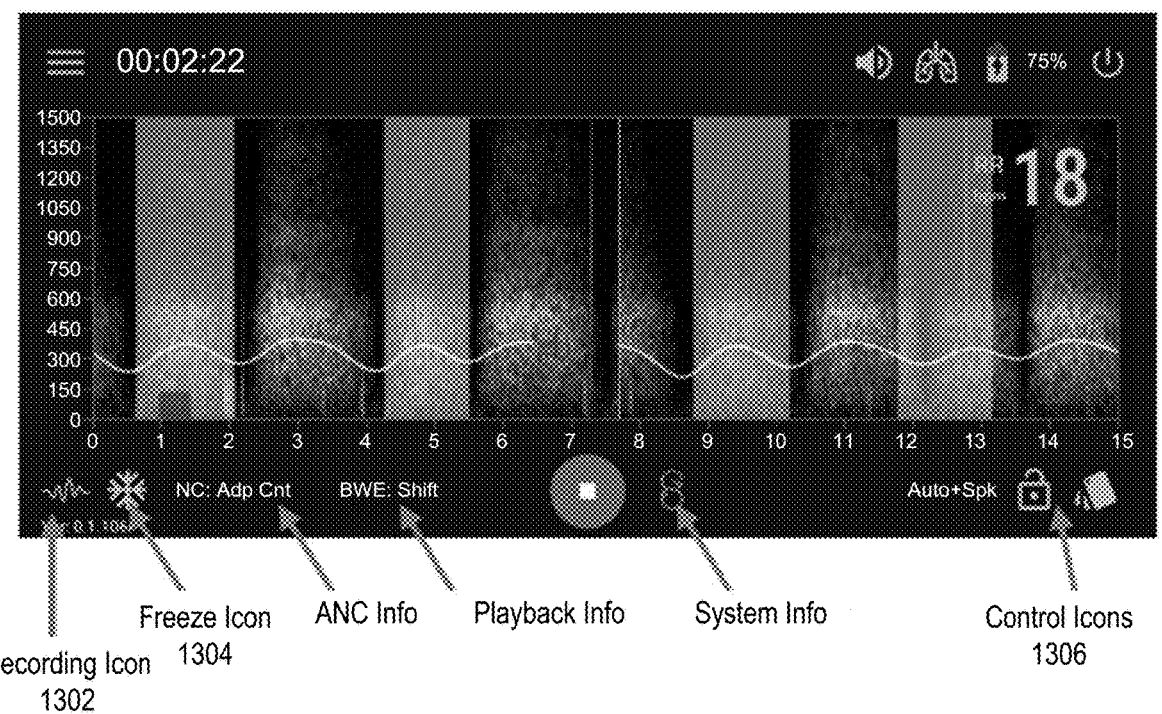
FIG. 13B illustrates how digital elements (also referred to as "graphical elements") may overlay the spectrogram to provide additional insight into the health of a patient.

FIGS. 13A-B include examples of interfaces that may be generated by the diagnostic platform. FIG. 13A illustrates how the spectrogram produced by the diagnostic platform may be presented in near real time to facilitate diagnostic determination by a healthcare professional. Meanwhile, FIG. 13B illustrates how digital elements (also referred to as "graphical elements") may overlay the spectrogram to provide additional insight into the health of the patient. Here, for example, vertical bands overlay the portions of the spectrogram that the diagnostic platform has determined correspond to breathing events. Note that in some embodiments, these vertical bands cover an entire breathing cycle (i.e., inhalation and exhalation), while in other embodiments these vertical bands cover only a portion of the breathing cycle (e.g., only inhalation).

The respiratory rate may be posted (e.g., in the upper-right corner) for review by a healthcare professional. In the event that the diagnostic platform determines that the respiratory rate is abnormal, then the posted value may be visually altered in some manner. For example, the posted value may be rendered in a different color, rendered at a different (e.g., larger) size), or periodically removed and then reposted so as to "flash" to draw the attention of the healthcare professional. The diagnostic platform may determine that the respiratory rate is abnormal if the value falls beneath a lower threshold (e.g., 4, 5, or 8) or exceeds an upper threshold (e.g., 35, 45, or 60), or the diagnostic platform may determine that the respiratory rate is abnormal if no breathing events have been discovered within a predetermined amount of time (e.g., 10, 15, or 20 seconds).

As shown in FIG. 13B, the interface may include various icons that are associated with different functionalities supported by the diagnostic platform. When selected, a recording icon 1302 may initiate recording of content shown on the interface. For example, the recording may include the spectrogram along with any digital elements, as well as the corresponding audio data. When selected, a freeze icon 1304 may freeze the interface as it is presently shown. Thus, additional content may not be posted to the interface when the freeze icon 1304 is selected. Content may be presented on the interface once again after the freeze icon 1304 has been selected another time. When selected, control icons 1306 may control various aspects of the interface. For example, the control icons 1306 may permit a healthcare professional to lock the interface (e.g., to semi-permanently or temporarily prevent further changes), change the layout of the interface, change the color scheme of the interface, change the input mechanism (e.g., touch versus voice) for the interface, and the like. Supplemental information may also be presented on the interface. In FIG. 13B, for example, the interface includes information regarding the state of active noise cancellation (ANC), playback, and connected electronic stethoscope system. Thus, a healthcare professional may be able to readily observe whether the computing device on which the diagnostic platform resides (and the interface is shown) is communicatively connected to the electronic stethoscope system that is responsible for generating the audio data.

Methodologies for Computing Respiratory Rate

Figure 14:
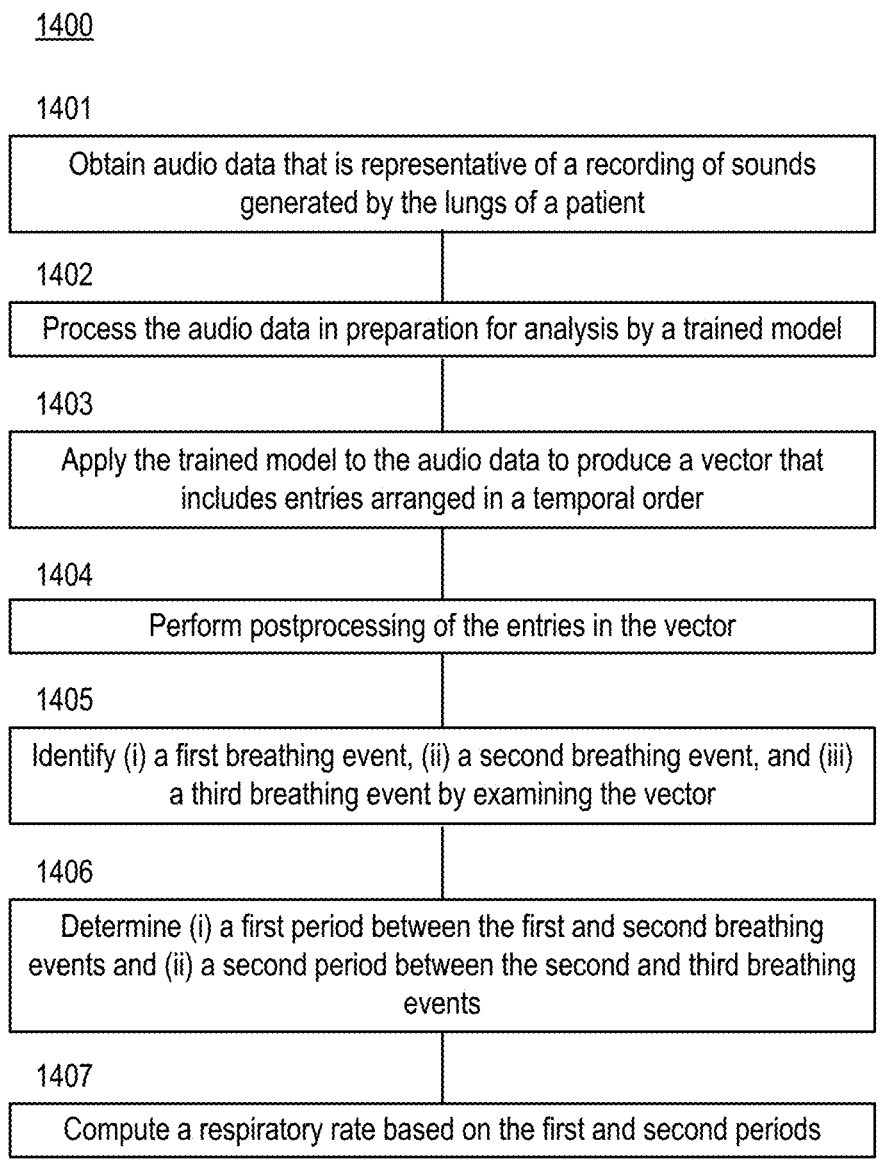
FIG. 14 depicts a flow diagram of a process for detecting breathing events through analysis of audio data and then computing the respiratory rate based on those breathing events.

FIG. 14 depicts a flow diagram of a process 1400 for detecting breathing events through analysis of audio data and then computing the respiratory rate based on those breathing events. Initially, a diagnostic platform can obtain audio data that is representative of a recording of sounds generated by the lungs of a patient (step 1401). In some embodiments, the diagnostic platform receives the audio data directly from an electronic stethoscope system. In other embodiments, the diagnostic platform acquires the audio data from a storage medium. For example, a patient may be permitted to upload audio data to the storage medium that she recorded herself. As another example, a healthcare professional may be permitted to upload audio data to the storage medium that she recorded herself.

The diagnostic platform can then process the audio data in preparation for analysis by a trained model (step 1402). For example, the diagnostic platform may apply a high-pass filter to the audio data and then generate, based on the filtered audio data, (i) a spectrogram, (ii) a series of MFCCs, and (iii) a series of values that are representative of energy summed across different frequency bands of the spectrogram. The diagnostic platform may concatenate these features into a feature matrix. More specifically, the diagnostic platform may concatenate the spectrogram, series of MFCCs, and series of values into a feature matrix that can be provided to the trained model as input. In some embodiments, the diagnostic platform performs min-max normalization on the feature matrix so that each entry has a value between zero and one.

Then, the diagnostic platform can apply the trained model to the audio data (or analyses of the audio data) to produce a vector that includes entries arranged in a temporal order (step 1403). More specifically, the diagnostic platform may apply the trained model to the feature matrix as mentioned above. Each entry in the vector may be representative of a detection, produced by the trained model, that indicates whether a corresponding segment of the audio data is representative of a breathing event. Each entry in the vector may correspond to a different segment of the audio data, though all entries in the vector may correspond to segments of the audio data of equal duration. Assume, for example, that the audio data obtained by the diagnostic platform is representative of a recording with a total duration of 15 seconds. As part of preprocessing, the recording may be split into 938 segments of equal duration. For each of these segments, the trained model may produce an output that is representative of a detection as to whether the corresponding portion of audio data is representative of a breathing event.

Thereafter, the diagnostic platform may perform postprocessing of the entries in the vector as mentioned above (step 1404). For example, the diagnostic platform may examine the vector identify a pair of entries corresponding to the same type of breathing event that are separated by less than a predetermined number of entries and then merge the pair of entries so as to indicate that the pair of entries are representative of a single breathing event. This may be done to ensure that a breathing event is not missed due to the presence of a segment for which the model indicated no breathing event. Additionally or alternatively, the diagnostic platform may examine the vector to identify a series of consecutive entries corresponding to the same type of breathing event that is less than a predetermined length and then adjust the label associated with each entry in the series of consecutive entries so as to delete a breathing event represented by the series of consecutive entries. This may be done to ensure that no breathing events less than a predetermined length (e.g., 0.25, 0.50, or 1.00 seconds) are recognized.

The diagnostic platform can then identify (i) a first breathing event, (ii) a second breathing event, and (iii) a third breathing event by examining the vector (step 1405). The second breathing event may follow the first breathing event, and the third breathing event may follow the second breathing event. Each breathing event may correspond to at least two consecutive entries in the vector that indicate the corresponding segments of the audio data are representative of a breathing event. The number of consecutive entries may correspond to the minimum length for breathing events that is enforced by the diagnostic platform.

Then, the diagnostic platform can determine (a) a first period between the first and second breathing events and (b) a second period between the second and third breathing events (step 1406). As discussed above, the first period may extend from the beginning of the first breathing event to the beginning of the second breathing event, and the second period may extend from the beginning of the second breathing event to the beginning of the third breathing event. The diagnostic platform can then compute the respiratory rate based on the first and second periods (step 1407). For example, the diagnostic platform may divide 120 by the sum of the first and second periods to establish the respiratory rate.

FIG. 15 depicts a flow diagram of a process 1500 for computing the respiratory rate based on analysis of audio data containing sounds made by the lungs of a patient. Initially, a diagnostic platform can obtain a vector that includes entries arranged in temporal order (step 1501). At a high level, each entry in the vector may be indicative of a detection regarding whether a corresponding segment of audio data is representative of a breathing event. As discussed above, the vector may be generated, as output, by a model that is applied to the audio data or analyses of the audio data by the diagnostic platform.

Then, the diagnostic platform can identify (i) a first breathing event, (ii) a second breathing event, and (iii) a third breathing event by examining the entries of the vector (step 1502). Normally, this is accomplished by examining the vector to identify consecutive entries that are associated with the same type of breathing event. For example, the diagnostic platform may parse the vector to identify consecutive entries with the same detection (e.g., "inhalation" or "no action" as shown in FIG. 9). Thus, each breathing event may correspond to a series of consecutive entries that (i) exceeds a predetermined length and (ii) indicates the corresponding segments of the audio data are representative of a breathing event. As discussed above, the diagnostic platform may perform postprocessing to ensure that false positives and negatives do not impact its ability to identify breathing events.

The diagnostic platform can then determine (a) a first period between the first and second breathing events and (b) a second period between the second and third breathing events (step 1503). Step 1503 of FIG. 15 may be similar to step 1406 of FIG. 14. Thereafter, the diagnostic platform can compute the respiratory rate based on the first and second periods (step 1504). For example, the diagnostic platform may divide 120 by the sum of the first and second periods to establish the respiratory rate.

In some embodiments, the diagnostic platform is configured to cause display of an interface that includes a spectrogram corresponding to the audio data (step 1505). Examples of such interfaces are shown in FIGS. 13A-B. In such embodiments, the diagnostic platform may post the respiratory rate to the interface to facilitate diagnostic determination by a healthcare professional (step 1506). Moreover, the diagnostic platform may compare the respiratory rate to a threshold as discussed above (step 1507) and then take appropriate action based on an outcome of the comparison (step 1508). For example, if the diagnostic platform determines that the respiratory rate falls beneath a lower threshold, the diagnostic platform may generate a notification indicating as much. Similarly, if the diagnostic platform determines that the respiratory rate exceeds an upper threshold, the diagnostic platform may generate a notification indicating as much. Normally, the notification is presented on the interface on which the respiratory rate is posted. For example, the respiratory rate may be visually altered responsive to a determination that it falls beneath the lower threshold or exceeds the upper threshold.

Unless contrary to physical possibility, it is envisioned that the steps described above may be performed in various sequences and combinations.

For example, the process 1500 may be performed repeatedly so that the respiratory rate is continually recomputed as additional breathing events are discovered. However, as mentioned above, the diagnostic platform may be programmed to increment the denominator (and thus decrease the respiratory rate) if no breathing events are discovered.

As another example, the respiratory rate may be computed using more than two periods. Generally, computing the respiratory rate using a single period is undesirable as the value will vary too much over relatively short periods of time to be helpful to healthcare professionals. However, the diagnostic platform could compute the respiratory rate using three or more periods. Assume, for example, that the diagnostic platform is tasked with computing the respiratory rate using three periods defined by four breathing events. In such a scenario, the diagnostic platform may perform steps largely as described above with reference to FIGS. 14-15. However, the diagnostic platform will then divide 180 by the sum of the first, second, and third periods. While the process remains largely the same, to compute the respiratory rate, the diagnostic platform will divide 60 times "N," where "N" is the number of periods, by the sum of those "N" periods.

Other steps may also be included in some embodiments. For example, diagnostically relevant insights, such as the presence of breathing abnormalities, could be posted to an interface (e.g., the interface of FIG. 13B) or stored in a data structure that is representative of a profile associated with the patient. Thus, diagnostically relevant insights may be stored in data structures that are encoded with audio data associated with the corresponding patients.

Exemplary Use Case of Electronic Stethoscope System and Diagnostic Platform

The demand for moderate to severe anesthesia has gradually become greater than traditional intubation surgery, and anesthesia has become a mainstream treatment in healthcare facilities. The risk of respiratory arrest or airway obstruction still cannot be eliminated, however. There is a lack of direct and continuous monitoring of the respiratory status of patients, and the auscultation-driven approaches discussed above represent a solution to this problem.

According to the Surgical Safety Guidance published by the World Health Organization (WHO), moderate non-intubated anesthesia requires consistent monitoring by the attending healthcare professional. This has traditionally been accomplished in several ways, including confirming ventilation based on auscultation, monitoring end-tidal $CO_2$, or verbally communicating with the patient. But these traditional approaches are impractical, if not impossible, in many situations.

The auscultation-driven approach discussed above can be employed in situations that are unsuitable for these traditional approaches. For example, the auscultation-driven approach may be used in situations such as plastic surgery, gastrointestinal endoscopic examinations, and dental procedures where sedation is often used to lessen pain. As another example, the auscultation-driven approach may be used in situations where there is a high risk of disease transmission (e.g., treatment of patients that have respiratory illnesses). One of the most important applications of the approaches described herein is the ability to quickly find that the airway has become obstructed through auscultation. Together, the electronic stethoscope system and diagnostic platform allow healthcare professionals to continuously monitor the patient without needing to manually evaluate her breathing sounds.

A. Plastic Surgery

Certain procedures, such as rhinoplasty, will prevent end-tidal $CO_2$ from being used to monitor the respiratory state as those patients will be unable to wear the necessary mask. Peripheral oximeters possess an intrinsic latency and are only able to generate notifications when the oxygen desaturates below a certain level.

B. Gastrointestinal Endoscopy

Traditionally, peripheral oximeters and end-tidal $CO_2$ monitors have been used to monitor the respiratory status of patients during gastrointestinal endoscopies. These two approaches possess an intrinsic latency and provide notifications only when oxygen desaturation or end-tidal volume changes at least a certain amount.

C. Dental Procedures

During dental procedures, it is difficult for healthcare professionals to continually monitor vital signs. Not only is a high degree of concentration required, but it is not unusual for only one or two healthcare professionals to be present while a dental procedure is performed. Moreover, patients can easily gag or choke on their own saliva, which is especially risky if those patients are under the effects of anesthesia.

D. Epidemic Prevention

To prevent transmission of diseases, patients are often isolated. When isolation is necessary, it may be dangerous for healthcare professionals to perform traditional auscultation. Moreover, healthcare professionals may be unable to administrate auscultation while wearing personal protective equipment (PPE) such as protective gowns and masks. Simply put, the combination of isolation plus PPE can make it difficult to properly evaluate the respiratory state of patients.

Figure 16:
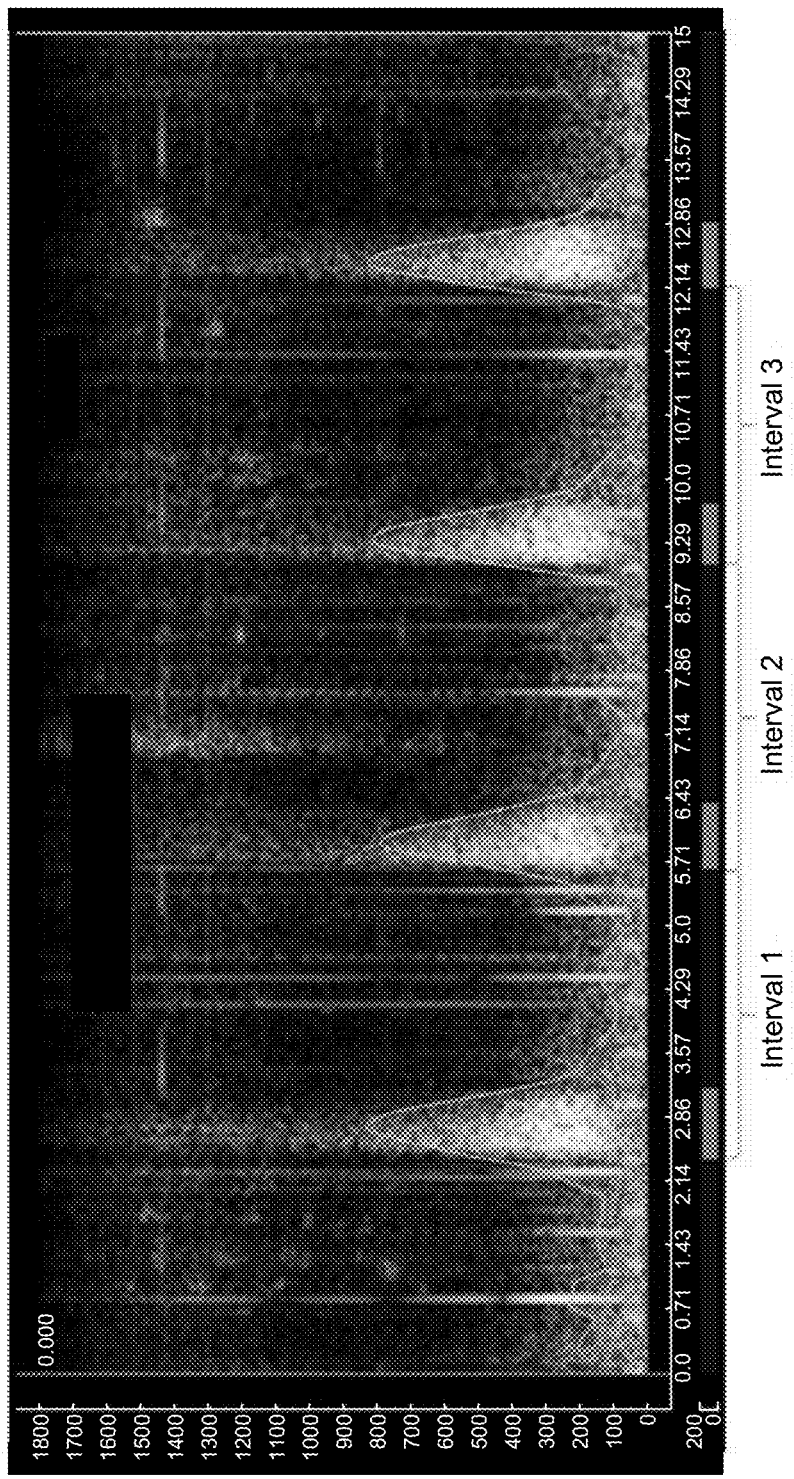
FIG. 16 illustrates how the electronic stethoscope systems and diagnostic platforms described herein can be used by healthcare professionals to hear auscultation sounds and see the breathing events in near real time.

The electronic stethoscope system and diagnostic platform can be used to not only provide a means for visualizing breathing events, but also initiate playback of auscultation sounds and generate instantaneous notifications. Healthcare professionals can hear the auscultation sounds and see the breathing events as shown in FIG. 16, which can be used to establish when the airway has become partially obstructed or when the respiratory rate has become unstable.

Processing System

Figure 17:
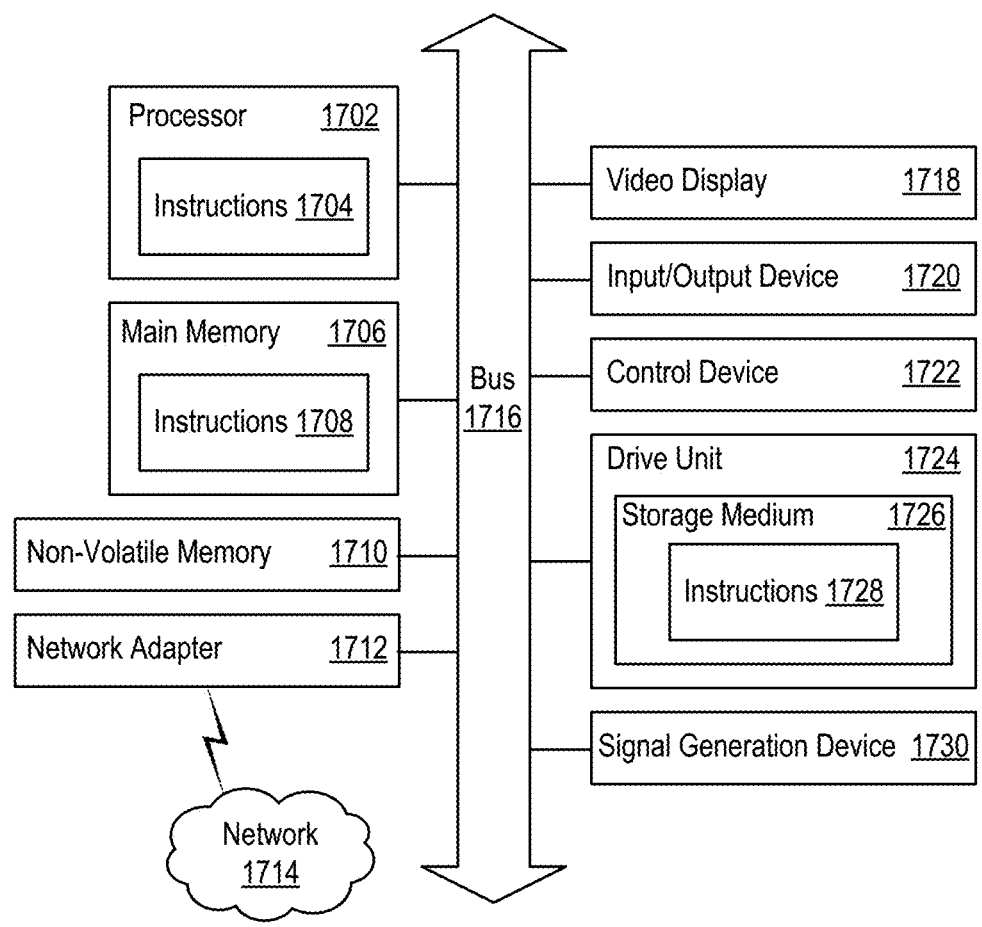
FIG. 17 is a block diagram illustrating an example of a processing system in which at least some operations described herein can be implemented.

FIG. 17 is a block diagram illustrating an example of a processing system 1700 in which at least some operations described herein can be implemented. For example, components of the processing system 1700 may be hosted on a computing device that executes a diagnostic platform. Examples of computing devices include electronic stethoscope systems, mobile phones, tablet computers, personal computers, and computer servers.

The processing system 1700 may include a processor 1702, main memory 1706, non-volatile memory 1710, network adapter 1712 (e.g., a network interface), video display 1718, input/output device 1720, control device 1722 (e.g., a keyboard, pointing device, or mechanical input such as a button), drive unit 1724 that includes a storage medium 1726, and signal generation device 1730 that are communicatively connected to a bus 1716. The bus 1716 is illustrated as an abstraction that represents one or more physical buses and/or point-to-point connections that are connected by appropriate bridges, adapters, or controllers. The bus 1716, therefore, can include a system bus, Peripheral Component Interconnect (PCI) bus, PCI-Express bus, Hyper-Transport bus, Industry Standard Architecture (ISA) bus, Small Computer System Interface (SCSI) bus, USB, Inter-Integrated Circuit ($I^2C$) bus, or a bus compliant with Institute of Electrical and Electronics Engineers (IEEE) Standard 1394.

The processing system 1700 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 1700.

While the main memory 1706, non-volatile memory 1710, and storage medium 1726 are shown to be a single medium, the terms "storage medium" and "machine-readable medium" should be taken to include a single medium or multiple media that stores one or more sets of instructions 1728. The terms "storage medium" and "machine-readable medium" should also be taken to include any medium that is capable of storing, encoding, or carrying a set of instructions for execution by the processing system 1700.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 1704, 1708, 1728) set at various times in various memories and storage devices in a computing device. When read and executed by the processor 1702, the instructions cause the processing system 1700 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile memory, non-volatile memory 1710, removable disks, hard disk drives (HDDs), optical disks (e.g., compact disc read-only memory (CD-ROMs) and Digital Versatile Discs (DVDs)), cloud-based storage, and transmission-type media such as digital and analog communication links.

The network adapter 1712 enables the processing system 1700 to mediate data in a network 1714 with an entity that is external to the processing system 1700 through any communication protocol supported by the processing system 1700 and the external entity. The network adapter 1712 can include a network adapter card, a wireless network interface card, a switch, a protocol converter, a gateway, a bridge, a hub, a receiver, a repeater, or a transceiver that includes an integrated circuit (e.g., enabling communication over Bluetooth or Wi-Fi).

REMARKS

The foregoing description of various embodiments of the technology has been provided for the purposes of illustration and description. It is not intended to be exhaustive or to limit the claimed subject matter to the precise forms disclosed.

Many modifications and variations will be apparent to those skilled in the art. Embodiments were chosen and described in order to best describe the principles of the technology and its practical applications, thereby enabling others skilled in the relevant art to understand the claimed subject matter, the various embodiments, and the various modifications that are suited to the particular uses contemplated.

What is claimed is:

1. A method for computing a respiratory rate, the method comprising:
    obtaining audio data that is representative of a recording of sounds generated by the lungs of a patient;
    processing the audio data in preparation for analysis by a trained model by—
        applying a high-pass filter to the audio data,
        generating, based on the audio data, (i) a spectrogram, (ii) a series of Mel-frequency cepstral coefficients (MFCCs), and (iii) a series of values representative of energy summed across different frequency bands of the spectrogram, and
        concatenating the spectrogram, the series of MFCCs, and the series of values into a feature matrix;
    applying the trained model to the audio data to produce a vector that includes entries arranged in temporal order, wherein each entry in the vector indicates whether a corresponding segment of the audio data is representative of a breathing event;
    identifying (i) a first breathing event, (ii) a second breathing event that follows the first breathing event, and (iii) a third breathing event that follows the second breathing event by examining the vector;
    determining (a) a first period between the first and second breathing events and (b) a second period between the second and third breathing events; and
    computing a respiratory rate based on the first and second periods by dividing 120 by a sum of the first and second periods.

2. The method of claim 1, wherein each entry in the vector corresponds to a different segment of the audio data, and wherein all entries in the vector correspond to segments of the audio data of equal duration.

3. The method of claim 1, wherein each breathing event corresponds to at least two consecutive entries in the vector that indicate the corresponding segments of the audio data are representative of a breathing event.

4. The method of claim 1, wherein said processing further comprises:
    performing min-max normalization on the feature matrix so that each entry has a value between zero and one.

5. The method of claim 1, wherein a cut-off frequency of the high-pass filter causes sounds made by another internal organ of the patient to be filtered from the audio data.

6. The method of claim 1, further comprising:
    examining the vector to identify a pair of entries corresponding to a same type of breathing event that are separated by less than a predetermined number of entries; and
    merging the pair of entries so as to indicate that the pair of entries are representative of a single breathing event.

7. The method of claim 6, wherein the pair of entries indicate that the corresponding segments of the audio data are representative of an inhalation.

8. The method of claim 6, wherein the pair of entries indicate that the corresponding segments of the audio data are representative of an exhalation.

9. The method of claim 1, further comprising:
- examining the vector to identify a series of consecutive entries corresponding to a same type of breathing event that is less than a predetermined length; and
- adjusting a label associated with each entry in the series of consecutive entries so as to delete a breathing event represented by the series of consecutive entries.

* * * * *